(12) United States Patent
Wang et al.

(10) Patent No.: US 11,884,738 B2
(45) Date of Patent: Jan. 30, 2024

(54) METHODS AND COMPOSITIONS FOR ACTIVATION OF T CELLS USING NANOPARTICLES CONJUGATED WITH MULTIPLE LIGANDS FOR BINDING RECEPTORS ON T CELLS

(71) Applicant: The University of North Carolina at Chapel Hill, Chapel Hill, NC (US)

(72) Inventors: Andrew Wang, Durham, NC (US); Yu Mi, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 15/938,999

(22) Filed: Mar. 28, 2018

(65) Prior Publication Data

US 2018/0282423 A1 Oct. 4, 2018

Related U.S. Application Data

(60) Provisional application No. 62/479,665, filed on Mar. 31, 2017.

(51) Int. Cl.
| | |
|---|---|
| A61K 47/50 | (2017.01) |
| C07K 16/28 | (2006.01) |
| A61K 39/395 | (2006.01) |
| A61K 45/06 | (2006.01) |
| C07K 16/30 | (2006.01) |
| A61K 47/69 | (2017.01) |
| A61P 35/00 | (2006.01) |
| A61K 39/00 | (2006.01) |

(52) U.S. Cl.
CPC ...... *C07K 16/2878* (2013.01); *A61K 39/3955* (2013.01); *A61K 45/06* (2013.01); *A61K 47/6935* (2017.08); *A61K 47/6937* (2017.08); *A61P 35/00* (2018.01); *C07K 16/2818* (2013.01); *C07K 16/30* (2013.01); *A61K 2039/505* (2013.01); *C07K 2317/54* (2013.01); *C07K 2317/55* (2013.01); *C07K 2317/622* (2013.01); *C07K 2317/75* (2013.01); *C07K 2317/76* (2013.01)

(58) Field of Classification Search
CPC ............ C07K 16/2878; C07K 16/2818; C07K 2317/75; A61K 47/6937
See application file for complete search history.

(56) References Cited

U.S. PATENT DOCUMENTS

| | | | | |
|---|---|---|---|---|
| 2014/0377334 A1* | 12/2014 | Irwine | .................. | A61K 9/1271 424/490 |
| 2015/0190506 A1* | 7/2015 | Cheung | ............... | C07K 16/2878 424/134.1 |
| 2016/0339091 A1* | 11/2016 | Powell | ................ | A61K 39/0011 |
| 2018/0221508 A1* | 8/2018 | Kadiyala | ............ | A61K 47/6849 |
| 2019/0175755 A1* | 6/2019 | Kosmides | ............ | A61K 9/0019 |
| 2020/0179528 A9* | 6/2020 | Goldberg | ........... | C07K 16/2818 |

OTHER PUBLICATIONS

Kosmides et al (Journal for ImmunoTherapy of Cancer, 2014, 2: (Suppl 3):P108).*
Chen et al (Cellular Immunology, 2014, 287:91-99).*
Montler et al (Clinical & Translational Immunology, 2016, 5:e70, internet pp. 1-8).*
Stintzing (F1000Prime Reports, 2014, 6:108, internet pp. 1-12).*
Werengowska-Ciecwierz et al (Advances in Condensed Matter Physics, 2015, p. 1-27).*
Shi et al (Journal of Materials Chemistry, 2009, 19:5485-5498).*
Hassane et al (Bioconjugate Chem. 2006, 17:849-854).*
Zander et al (2015, Cell Host & Microbe, 17:628-641).*
McGray et al (American Society of Gene & Cell Therapy, 2014, 22:206-218).*
Moynihan et al (Nature Medicine, 2016, 22:1402-1410).*
Cheng et al (Genetic Engineering & Biotechnology News, May 2016, vol. 36, No. 9, p. 16-17; internet pp. 1-6).*
Chauvin et al (Journal of Clinical Investigation, 2015, 125:2046-2058).*
Duraiswamy et al (Cancer Research, 2013, 73:3591-3603).*
Selby et al (Journal of Clinical Oncology, 2013, 31, No. 15_suppl, abstract 3061).*
Mi et al (Proceedings of the American Association for Cancer Research Annual Meeting 2017; Apr. 1-5, 2017; Washington, DC. Philadelphia (PA): AACR; Cancer Res 2017;77(13 Suppl):Abstract nr 978).*
Shrimali et al (Cancer Immunology Research, Aug. 2017; 5:755-766).*
Asaoka et al. "PD-1 Blockade in Tumors with Mismatch-Repair Deficiency" The New England Journal of Medicine, 373:1979 (2015).
Barker et al. "The tumour microenvironment after radiotherapy: mechanisms of resistance and recurrence" Nature reviews. Cancer, 15:409-425 (2015).
Chen et al. "Molecular mechanisms of T cell co-stimulation and co-inhibition" Nature Reviews. Immunology, 13 (4):227-242 (2013).
Cheng et al. "Formulation of functionalized PLGA-PEG nanoparticles for in vivo targeted drug delivery" Biomaterials, 28:869-876 (2007).
Garon et al. "Pembrolizumab for the treatment of non-small-cell lung cancer" The New England Journal of Medicine, 372:2018-2028 (2015).
Gubin et al. "Checkpoint blockade cancer immunotherapy targets tumour-specific mutant antigens" Nature, 515:577-581 (2014).
Harris et al. "Immuno-oncology combinations: raising the tail of the survival curve" Cancer Biology & Medicine, 13 (2):171-193 (2016).
Hoyle et al. "Thiol-click chemistry: a multifaceted toolbox for small molecule and polymer synthesis" Chemical Society Reviews, 39:1355-1387 (2010) (Abstract only).
Jiang et al. "T-cell exhaustion in the tumor microenvironment" Cell Death & Disease, 6:e1792 (2015).
Khalil et al. "The future of cancer treatment: immunomodulation, CARs and combination immunotherapy" Nature Reviews. Clinical Oncology, 13(5):273-290 (2016).

(Continued)

*Primary Examiner* — Laura B Goddard
(74) *Attorney, Agent, or Firm* — Myers Bigel, P.A.

(57) ABSTRACT

The present invention provides methods and compositions comprising a particle comprising at least two different targeting agents that each bind a different protein receptor on a T cell surface.

16 Claims, 29 Drawing Sheets

(56) References Cited

OTHER PUBLICATIONS

Kwong et al. "Induction of potent anti-tumor responses while eliminating systemic side effects via liposome-anchored combinatorial immunotherapy" Biomaterials, 32(22):5134-5147 (2011).

Kwong et al. "Localized immunotherapy via liposome-anchored Anti-CD137 + IL-2 prevents lethal toxicity and elicits local and systemic antitumor immunity" Cancer Research, 73:1547-1558 (2013).

Mahoney et al. "Combination cancer immunotherapy and new immunomodulatory targets" Nature Reviews. Drug Discovery, 14:561-584 (2015) (Abstract only).

Melero et al. "Therapeutic vaccines for cancer: an overview of clinical trials" Nature reviews. Clinical Oncology, 11:509-524 (2014).

Melero et al. "Evolving synergistic combinations of targeted immunotherapies to combat cancer" Nature reviews. Cancer, 15:457-472 (2015).

Mellman et al. "Cancer immunotherapy comes of age" Nature, 480(7378):480-489 (2011).

Mi et al. "Abstract 978: Spatial-temporal delivery of OX40 agonist and PD-1 inhibitor using nanoparticles improves therapeutic efficacy of cancer immunotherapy" Cancer Research (2 pages) Proceedings: AACR Annual Meeting, Washington, DC; Apr. 1-5, 2017.

Motzer et al. "Nivolumab versus Everolimus in Advanced Renal-Cell Carcinoma" The New England Journal of Medicine, 373:1803-1813 (2015).

Pardoll, Drew M. "The blockade of immune checkpoints in cancer immunotherapy" Nature reviews. Cancer, 12:252-264 (2012).

Rizvi et al. "Cancer immunology. Mutational landscape determines sensitivity to PD-1 blockade in non-small cell lung cancer" Science, 348(6230):124-128 (2015).

Rodriguez-Ruiz et al. "Abscopal Effects of Radiotherapy Are Enhanced by Combined Immunostimulatory mAbs and Are Dependent on CD8 T Cells and Crosspriming" Cancer Research, 76:5994-6005 (2016).

Sallusto et al. "Central memory and effector memory T cell subsets: function, generation, and maintenance" Annual Review of Immunology, 22:745-763 (2004) (Abstract only).

Sharma et al. "The future of immune checkpoint therapy" Science, 348:56-61 (2015) (Abstract only).

Tran et al. "Cancer immunotherapy based on mutation-specific CD4+ T cells in a patient with epithelial cancer" Science, 344:641-645 (2014) (Abstract only).

Twyman-Saint Victor et al. "Radiation and dual checkpoint blockade activate non-redundant immune mechanisms in cancer" Nature, 520:373-377 (2015).

Wherry, E. J. "T cell exhaustion" Nature Immunology, 12(6):492-499 (2011).

\* cited by examiner

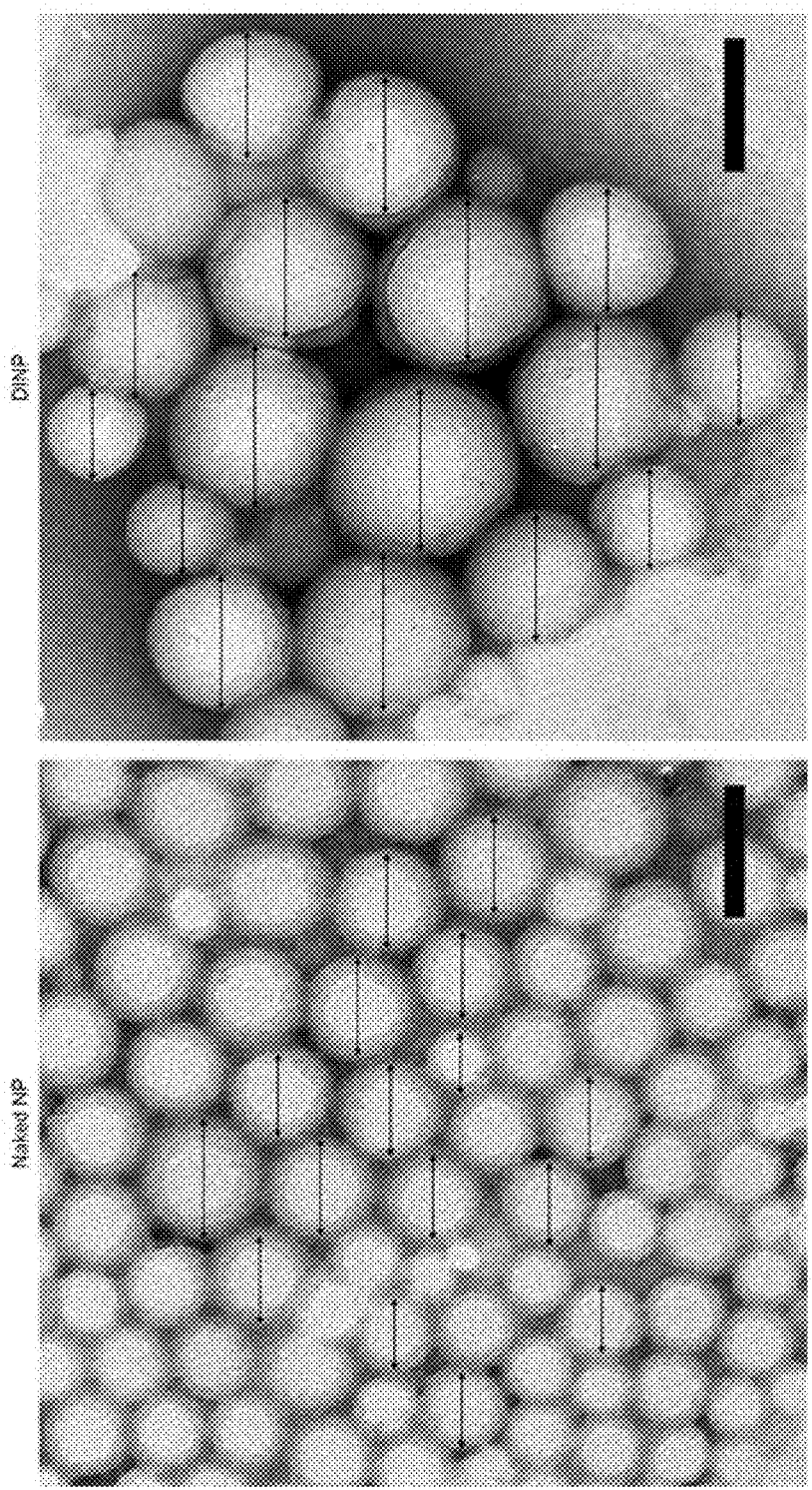

METHODS AND COMPOSITIONS FOR ACTIVATION OF T CELLS USING NANOPARTICLES CONJUGATED WITH MULTIPLE LIGANDS FOR BINDING RECEPTORS ON T CELLS

PRIORITY STATEMENT

This application claims the benefit, under 35 U.S.C. § 119(e), of U.S. Provisional Application Ser. No. 62/479,665, filed Mar. 31, 2017, the entire contents of which are incorporated by reference herein.

STATEMENT OF GOVERNMENT SUPPORT

This invention was made with government support under Grant Numbers CA198999 and CA178748 awarded by the National Institutes of Health. The government has certain rights in the invention.

FIELD OF THE INVENTION

The present invention relates to immunoregulation and cancer immunotherapy.

BACKGROUND OF THE INVENTION

Combination immunotherapy has recently emerged as a powerful cancer treatment strategy. Clinical data suggest that the most effective immunotherapy regimens combine therapeutics that work synergistically to improve T cell activation. Unfortunately, current efforts have shown that co-administration of these immunotherapy therapeutics as free antibodies has resulted in suboptimal T cell binding events with only a subset of the T cells binding both aPD-1 and aOX40 simultaneously. Thus, it would be highly desirable to develop immunotherapy agents that efficiently bind aPD-1 and aOX40 to T-cells simultaneously.

The present invention overcomes previous shortcomings in the art by providing compositions and methods of their use in immunotherapy.

SUMMARY OF THE INVENTION

In one embodiment, the present invention provides a particle, which can be a microparticle or nanoparticle, comprising at least two different targeting agents that each bind a different protein receptor on a T cell surface.

The present invention further provides a composition comprising the particle and a pharmaceutically acceptable carrier.

The present invention further provides a method of activating a T cell, comprising contacting the T cell with the particle or with the composition of this invention, under conditions whereby each different targeting agent can bind its respective protein receptor on the T cell surface.

In additional embodiments, the present invention provides a method of inducing a T cell immune response, comprising contacting the T cell with the particle or with the composition of this invention, under conditions whereby each different targeting agent can bind its respective protein receptor on the surface of the same T cell.

Further provided herein is a method of treating cancer in a subject in need thereof, comprising administering to the subject an effective amount of the particle or the composition of this invention, under conditions whereby each different targeting agent can bind its respective protein receptor on the surface of the same T cell.

Additionally, provided herein is a kit comprising the particle and/or the composition of and instructions for use.

These and other aspects of the invention are addressed in more detail in the description of the invention set forth below.

BRIEF DESCRIPTION OF THE DRAWINGS

FIGS. 1A-G: Dual immunotherapy nanoparticles (DINPs) conjugated with aPD-1 and aOX40 bind to their target ligands simultaneously. (1A) Schematic depicting DINPs facilitate enhancement of combination immunotherapy. (1B, 1C) Quantification of nanoparticle size and zeta potential change following DINP fabrication. (1D, 1E, 1F) Quantification of nanoparticle size using transmission electron microscopy (TEM) images. Data represents mean±standard deviation (SD) (n=16), Scale bar, 100 nm. (1G) Flow cytometric analysis assessing the ability of DINPs to bind to OX40 and PD1 ligands.

DETAILED DESCRIPTION OF THE INVENTION

Figure 1A:
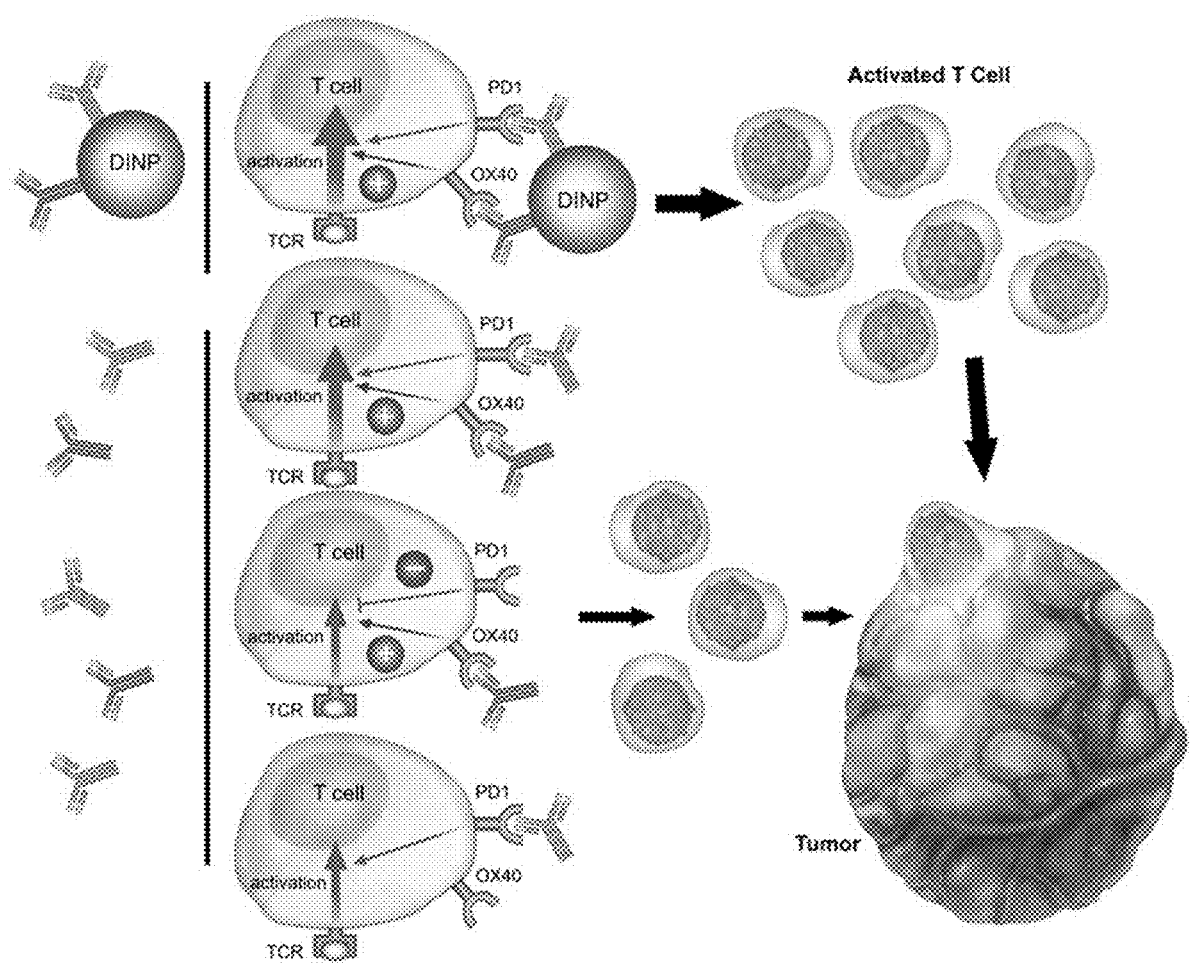

The present subject matter will be now be described more fully hereinafter with reference to the accompanying EXAMPLES, in which representative embodiments of the presently disclosed subject matter are shown. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for cloning genes, amplifying and detecting nucleic acids, and the like. Such techniques are known to those skilled in the art. See, e.g., Sambrook et al., Molecular Cloning: A Laboratory Manual 2nd Ed. (Cold Spring Harbor, NY, 1989); Ausubel et al. Current Protocols in Molecular Biology (Green Publishing Associates, Inc. and John Wiley & Sons, Inc., New York).

All publications, patent applications, patents, accession numbers and other references mentioned herein are incorporated by reference herein in their entirety.

While the following terms are believed to be well understood by one of ordinary skill in the art, the following definitions are set forth to facilitate explanation of the presently disclosed subject matter.

Following long-standing patent law convention, the terms "a" and "an" and "the" can mean one or more than one when used in this application, including the claims.

Unless otherwise indicated, all numbers expressing quantities of size, biomarker concentration, probability, percentage, and so forth used in the specification and claims are to be understood as being modified in all instances by the term "about." For example, the amounts can vary by about 10%, 5%, 1%, or 0.5%. Accordingly, unless indicated to the contrary, the numerical parameters set forth in this specification and attached claims are approximations that can vary depending upon the desired properties sought to be obtained by the presently disclosed subject matter.

The term "and/or" when used in describing two or more items or conditions refers to situations where all named items or conditions are present or applicable, or to situations wherein only one (or less than all) of the items or conditions is present or applicable. Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even ±0.1% of the specified amount.

As used herein, the term "comprising," which is synonymous with "including," "containing," and "characterized by," is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising," "consisting essentially of," and "consisting of," where one of these three terms is used herein, the presently disclosed subject matter can include the use of any of the other terms.

As used herein, the terms "subject" and "patient" are used interchangeably herein and refer to both human and nonhuman animals. A subject of this invention can be any subject that is susceptible to a disorder that can benefit by the methods and compositions of the present invention and/or be treated for a disorder by the methods and compositions of the present invention and in particular embodiments, the subject of this invention is a human subject.

A "subject in need thereof" or "a subject in need of" is a subject known to have, or is suspected of having or developing or is at risk of having or developing disorder that can be treated by the methods and compositions of the present invention.

The term "administering" or "administered" as used herein is meant to include topical, parenteral and/or oral administration, all of which are described herein. Parenteral administration includes, without limitation, intravenous, subcutaneous and/or intramuscular administration (e.g., skeletal muscle or cardiac muscle administration). It will be appreciated that the actual method and order of administration will vary according to, inter alia, the particular preparation of compound(s) being utilized, and the particular formulation(s) of the one or more other compounds being utilized. The optimal method and order of administration of the compositions of the invention for a given set of conditions can be ascertained by those skilled in the art using conventional techniques and in view of the information set out herein.

The term "administering" or "administered" also refers, without limitation, to oral, sublingual, buccal, transnasal, transdermal, rectal, intramuscular, intravenous, intraarterial (intracoronary), intraventricular, intrathecal, and subcutaneous routes. In accordance with good clinical practice, the instant compounds can be administered at a dose that will produce effective beneficial effects without causing undue harmful or untoward side effects, i.e., the benefits associated with administration outweigh the detrimental effects.

Also as used herein, the terms "treat," "treating" or "treatment" refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, and/or change in clinical parameters of the condition, disorder, disease or illness, etc., as would be well known in the art.

Additionally as used herein, the terms "proactive," "prevent," "preventing" or "prevention" refer to any type of action that results in the absence, avoidance and/or delay of the onset and/or progression of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

An "effective amount" or "therapeutically effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an effective amount or therapeutically effective amount in any individual case can be determined by one of ordinary skill in the art by reference to the pertinent texts and literature and/or by using routine experimentation. (See, for example, Remington, The Science and Practice of Pharmacy (latest edition)).

The term "biologically active" as used herein means an enzyme or protein having structural, regulatory, or biochemical functions of a naturally occurring molecule.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed.

Subjects with which the present invention is concerned include any subject susceptible to a disorder of this invention and are, in general, mammalian subjects, including humans, dogs, cats, and horses. The subjects may be of any gender, any ethnicity and any age.

"Therapeutically effective amount" or "treatment effective amount" as used herein refers to the amount of composition of this invention determined to produce a therapeutic response in a subject. Such therapeutically effective amounts are readily ascertained by one of ordinary skill in the art.

"Amino acid sequence" and terms such as "peptide," "polypeptide," and "protein" are used interchangeably herein, and are not meant to limit the amino acid sequence to the complete, native amino acid sequence (i.e., a sequence containing only those amino acids found in the protein as it occurs in nature) associated with the recited protein molecule. The proteins and protein fragments of the presently disclosed subject matter can be produced by recombinant approaches or can be isolated from a naturally occurring source. The protein fragments can be any size, and for example can range in size from four amino acid residues to the entire amino acid sequence minus one amino acid.

The terms "antibody" and "immunoglobulin" include antibodies or immunoglobulins of any isotype, fragments of antibodies that retain specific binding to antigen, including but not limited to Fab, Fv, single chain Fv (scFv), and Fd fragments, chimeric antibodies, humanized antibodies, single-chain antibodies, and fusion proteins including an antigen-binding portion of an antibody and a non-antibody protein. The antibodies can in some embodiments be detectably labeled, e.g., with a radioisotope, an enzyme which generates a detectable product, a fluorescent protein, and the like. The antibodies can in some embodiments be further conjugated to other moieties, such as members of specific binding pairs, e.g., biotin (member of biotin-avidin specific binding pair), and the like. Also encompassed by the terms are Fab', Fv, F(ab')$_2$, and other antibody fragments that retain specific binding to antigen (e.g., any antibody fragment that comprises at least one paratope).

Antibodies can exist in a variety of other forms including, for example, Fv, Fab, and (Fab')$_2$, as well as bi-functional (i.e., bi-specific) hybrid antibodies (see e.g., Lanzavecchia et al., 1987) and in single chains (see e.g., Huston et al., 1988 and Bird et al., 1988, each of which is incorporated herein by reference in its entirety). See generally, Hood et al., 1984, and Hunkapiller & Hood, 1986. The phrase "detection molecule" is used herein in its broadest sense to include any molecule that can bind with sufficient specificity to a biomarker to allow for detection of the particular biomarker. To allow for detection can mean to determine the presence or absence of the particular biomarker member and, in some embodiments, can mean to determine the amount of the particular biomarker. Detection molecules can include antibodies, antibody fragments, and nucleic acid sequences.

The current disclosure describes the utilization of nanoparticles that can deliver anti-OX40 and anti-PD1 antibodies simultaneously to T cells. Cancer immunotherapy is an exciting new approach to cancer treatment and there is strong interest in strategies to improve the long-term durable response rates of cancer immunotherapy. The current disclosure relates to the approach of combining checkpoint inhibitors such as a PD-1 with T cell activators such as OX40 agonists to further increase immune activation. Not to be bound by theory but it is believed that one can improve the therapeutic efficacy by temporally controlling the activation of OX40 and inhibiting PD-1 pathways. This approach is not limited to OX40 and PD-1 but also includes other cellular targets as listed in more detail herein.

In one embodiment, the present invention provides a particle, which can be a microparticle or nanoparticle, comprising at least two different targeting agents (e.g., aptamers, antibodies, antibody fragments, peptides, nanobodies) that each bind a different protein receptor on a T cell surface.

In some embodiments of the present invention, the particle comprises three different targeting agents that each bind a different protein receptor on a T cell surface.

In some embodiments of the present invention, the particle comprises four different targeting agents that each bind a different protein receptor on a T cell surface.

In some embodiments of the present invention, the particle of this invention can comprise more than four (e.g., 5, 6, 7, 8, 9, 10, 11, 12, 13, 14, 15, 16, 17, 18, 19, 20, etc.) different targeting agents that each bind a different protein receptor on a T cell surface.

In some embodiments of the present invention, the receptors on the T cell surface can be LFA-1, CD2, ICOS, CD28, CTLA-4, PD-1, HVEM, AITR, CD40L, CD27, 4-1BB, CD30, OX40, TCR, BTLA, DR3, GITR, SLAM, 2B4, TIM1, TIM2, TIM3, TIGIT, CD226, CD160, LAG3, LAIR1, B7-1, B7-H1, and any combination thereof, as well as any other receptor on a T cell surface that is now known or later identified. (See, e.g., Chen and Flies. "Molecular mechanisms of T cell co-stimulation and co-inhibition" *Nat. Rev. Immunol.*, 2013 Apr. 13(4): 227-242. doi:10.1038/nri3405.)

In some embodiments of the present invention, at least one of the targeting agents is an antibody or active fragment thereof.

In some embodiments of the present invention, each of the targeting agents is an antibody or active fragment thereof.

In some embodiments of the present invention, the antibody or active fragment is selected from the group consisting of a monoclonal antibody, a Fab fragment, a Fab'-SH fragment, a FV fragment, a single chain variable fragment (scFV) fragment, a (Fab')$_2$ fragment, and any combination thereof.

In some embodiments of the present invention, the particle comprises an antibody or active fragment thereof that specifically binds OX40 and an antibody or active fragment thereof that specifically binds PD-1.

In another embodiment, the present invention provides a composition comprising the particle and a pharmaceutically acceptable carrier.

In some embodiments, the present invention provides a method of activating a T cell, comprising contacting the T cell with the particle or with the composition, under conditions whereby each different targeting agent can bind the respective protein receptor on the T cell surface.

In some embodiments, the present invention provides a method of inducing a T cell immune response, comprising contacting the T cell with the particle or with the composition, under conditions whereby each different targeting agent can bind the respective protein receptor on the surface of the same T cell.

In some embodiments, the present invention provides a method of inducing a T cell immune response in a subject in need thereof, comprising administering to the subject an effective amount of the particle or the composition, under conditions whereby each different targeting agent can bind the respective protein receptor on the surface of the same T cell.

In some embodiments, the present invention provides a method of activating T cells in a subject in need thereof, comprising administering to the subject an effective amount of the particle or the composition, under conditions whereby each different targeting agent can bind the respective protein receptor on the surface of the same T cell.

In some embodiments, the present invention provides a method of treating cancer in a subject in need thereof, comprising administering to the subject an effective amount of the particle or the composition, under conditions whereby each different targeting agent can bind the respective protein receptor on the surface of the same T cell.

In some embodiments, the present invention provides a method of treating cancer in a subject in need thereof, wherein the cancer is selected from the group consisting of breast cancer, lung cancer, ovarian cancer, gastric cancer, bladder cancer, pancreatic cancer, endometrial cancer, uterine cancer, colon cancer, kidney cancer, esophageal cancer, prostate cancer, colorectal cancer, glioblastoma, neuroblastoma, Hodgkin's lymphoma, non-Hodgkin's lymphoma, multiple myeloma, liver cancer, skin cancer, blood cancer, and any combination thereof.

In some embodiments, the present invention provides a method of treating cancer in a subject (e.g., a subject in need thereof), wherein the subject has been diagnosed with cancer.

In some embodiments, the present invention provides a method of treating cancer in a subject (e.g., a subject in need thereof), wherein the particle or composition is administered via a route selected from the group consisting of intravenously, intramuscularly, subcutaneously, topically, orally, transdermally, intraperitoneally, intrathecally, intraventricularly, intraorbitally, intranasally, by implantation, by inhalation, intratumorally, and any combination thereof.

In some embodiments, the present invention provides a method of treating cancer in a subject in need thereof, further comprising the step of administering to the subject an effective amount of a chemotherapeutic agent and/or radiation therapy.

Pharmaceutical Compositions and Methods of Use

Exemplary Formulations. In certain embodiments, the invention also provides compositions comprising the particles of this invention together with one or more of the following: a pharmaceutically acceptable diluent; a carrier; a solubilizer; an emulsifier; a preservative; and/or an adjuvant. Such compositions may contain an effective amount of the particles. Thus, the use of the particles as provided herein in the preparation of a pharmaceutical composition or medicament is also included. Such compositions can be used in the treatment of a variety of diseases as described herein.

Acceptable formulation components for pharmaceutical preparations are nontoxic to recipients at the dosages and concentrations employed. In addition to the particles provided herein, compositions according to the invention may contain components for modifying, maintaining or preserving, for example, the pH, osmolarity, viscosity, clarity, color, isotonicity, odor, sterility, stability, rate of dissolution or release, adsorption or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants.

The primary vehicle or carrier in a pharmaceutical composition may be either aqueous or non-aqueous in nature. Suitable vehicles or carriers for such compositions include water (e.g., sterile water) for injection, physiological saline solution or artificial cerebrospinal fluid, possibly supplemented with other materials common in compositions for parenteral administration. Neutral buffered saline or saline mixed with serum albumin are further exemplary vehicles.

Compositions comprising particles of this invention may be prepared for storage by mixing the selected composition having the desired degree of purity with optional formulation agents in the form of a lyophilized cake or an aqueous solution. Further, the particles may be formulated as a lyophilizate using appropriate excipients such as sucrose.

Formulation components are present in concentrations that are acceptable to the site of administration. Buffers are advantageously used to maintain the composition at physiological pH or at a slightly lower pH, typically within a pH range of from about 4.0 to about 8.5, or alternatively, between about 5.0 to 8.0. Pharmaceutical compositions can comprise TRIS buffer of about pH 6.5-8.5, or acetate buffer of about pH 4.0-5.5, which may further include sorbitol or a suitable substitute therefor.

A pharmaceutical composition may involve an effective quantity of particles of this invention in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert materials, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions are in the form of sustained- or controlled-delivery formulations. Techniques for formulating a variety of other sustained- or controlled-delivery means, such as liposome carriers, bio-erodible microparticles or porous beads and depot injections can be. Sustained-release preparations may include semipermeable polymer matrices in the form of shaped articles, e.g., films, or microcapsules, polyesters, hydrogels, polylactides, copolymers of L-glutamic acid and gamma ethyl-L-glutamate, poly (2-hydroxyethyl-methacrylate), ethylene vinyl acetate or poly-D(−)-3-hydroxybutyric acid. Sustained release compositions may also include liposomes, which can be prepared by any of several methods known in the art.

The pharmaceutical composition to be used for in vivo administration typically is sterile. Sterilization may be accomplished by filtration through sterile filtration membranes. If the composition is lyophilized, sterilization may be conducted either prior to or following lyophilization and reconstitution. The composition for parenteral administration may be stored in lyophilized form or in a solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

The composition may be formulated for transdermal delivery, optionally with the inclusion of microneedles, microprojectiles, patches, electrodes, adhesives, backings, and/or packaging, or formulations for jet delivery, in accordance with known techniques. See, e.g., U.S. Pat. Nos. 8,043,250; 8,041,421; 8,036,738; 8,025,898; 8,017,146.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The present invention provides kits for producing multi-dose or single-dose administration units. For example, kits according to the invention may each contain both a first container having a dried composition and a second container having an aqueous diluent, including for example single and multi-chambered pre-filled syringes (e.g., liquid syringes, lyosyringes or needle-free syringes).

The pharmaceutical compositions of the invention can be delivered parenterally, typically by injection. Injections can be intraocular, intraperitoneal, intraportal, intramuscular, intravenous, intrathecal, intracerebral (intra-parenchymal), intracerebroventricular, intraarterial, intralesional, perilesional or subcutaneous. Eye drops can be used for intraocular administration. In some instances, injections may be localized to the vicinity of a particular bone or bones to which the treatment is targeted. For parenteral administration, the chimeric protein may be administered in a pyrogen-free, parenterally acceptable aqueous solution comprising the chimeric protein in a pharmaceutically acceptable vehicle. A particularly suitable vehicle for parenteral injection is sterile distilled water in which the chimeric proteins are formulated as a sterile, isotonic solution, properly preserved.

Pharmaceutical compositions comprising the particles of this invention may be administered by bolus injection and/or continuously by infusion, by implantation device, sustained release systems or other means for accomplishing prolonged release. The pharmaceutical composition also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous release. The preparation may be formulated with agent, such as injectable microspheres, bio-erodible particles, polymeric compounds (such as polylactic acid; polyglycolic acid; or copoly (lactic/glycolic) acid (PLGA), beads or liposomes, that can provide controlled or sustained release of the product which may then be delivered via a depot injection. Formulation with hyaluronic acid has the effect of promoting sustained duration in the circulation.

The subject compositions comprising particles of this invention may be formulated for inhalation. In these embodiments, the particles can be formulated as a dry powder for inhalation, or particle inhalation solutions may also be formulated with a propellant for aerosol delivery, such as by nebulization.

Certain pharmaceutical compositions of the invention can be delivered through the digestive tract, such as orally. The particles of this invention that are administered in this fashion may be formulated with or without those carriers customarily used in the compounding of solid dosage forms such as tablets and capsules. A capsule may be designed to release the active portion of the formulation at the point in the gastrointestinal tract when bioavailability is maximized and pre-systemic degradation is minimized. Additional agents can be included to facilitate absorption of the particles. For oral administration, modified amino acids may be used to confer resistance to digestive enzymes. Diluents, flavorings, low melting point waxes, vegetable oils, lubricants, suspending agents, tablet disintegrating agents, and binders may also be employed.

The subject compositions comprising particles also may be used ex vivo. In such instances, cells, tissues or organs that have been removed from the subject are exposed to or cultured with the particles. The cultured cells may then be implanted back into the subject or a different subject or used for other purposes.

In some embodiments, in order to decrease the chance of an immunological response, the particles of this invention may be encapsulated to avoid infiltration of surrounding tissues. Encapsulation materials are typically biocompatible, semi-permeable polymeric enclosures or membranes that allow the release of the particles but prevent the destruction of the cells by the patient's immune system or by other detrimental factors from the surrounding tissues.

B. Conditions for treatment. Subjects to be treated by the methods and compositions of the present invention include any afflicted with a disorder (e.g., cancer) or condition for which the methods and compositions of this invention would be beneficial and/or therapeutic.

C. Dosage. The pharmaceutical compositions that are provided can be administered for prophylactic and/or therapeutic treatments. An "effective amount" refers generally to an amount that is a sufficient, but non-toxic, amount of the active ingredient (i.e., particles of this invention) to achieve the desired effect, which, for example, can be a reduction or elimination in the severity and/or frequency of symptoms and/or improvement or remediation of damage. A "therapeutically effective amount" refers to an amount that is sufficient to remedy a disease state or symptoms, or otherwise prevent, hinder, retard or reverse the progression of a disease or any other undesirable symptom. A "prophylactically effective amount" refers to an amount that is effective to prevent, hinder or retard the onset of a disease state or symptom.

In general, toxicity and therapeutic efficacy of the particles of this invention can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred.

The data obtained from cell culture and/or animal studies can be used in formulating a range of dosages for subjects for treatment. The dosage of the active ingredient typically falls within a range of circulating concentrations that include the $ED_{50}$ with little or no toxicity. The dosage can vary within this range depending upon the dosage form employed and the route of administration utilized.

The effective amount of a pharmaceutical composition comprising particles of this invention to be employed therapeutically or prophylactically will depend, for example, upon the therapeutic context and objectives. One skilled in the art will appreciate that the appropriate dosage levels for treatment, according to certain embodiments, will thus vary depending, in part, upon the composition being delivered, the indication for which the particles are being used, the route of administration, and the size (body weight, body surface or organ size) and/or condition (the age and general health) of the subject. A clinician may titer the dosage and modify the route of administration to obtain the optimal therapeutic effect. Typical dosages for administration of the particles of this invention range from about 0.001 mg/kg to 2000 mg/kg. For example, in some embodiments, the particles can be administrated intravenously every one to three weeks.

The dosing frequency will depend upon the pharmacokinetic parameters of particles in the formulation. For example, a clinician will administer the composition until a dosage is reached that achieves the desired effect. The composition may therefore be administered as a single dose, or as two or more doses (which may or may not contain the same amount of the desired molecule) over time, or as a continuous infusion via an implantation device or catheter. Treatment may be continuous over time or intermittent. Further refinement of the appropriate dosage is routinely made by those of ordinary skill in the art and is within the ambit of tasks routinely performed by them. Appropriate dosages may be ascertained through use of appropriate dose-response data.

In some embodiments, the particles can be administered in combination with one or more other therapeutic agents and/or different therapies. Examples of therapeutic agents include, but are not limited to, anti-infectious agent (e.g., anti-septic agent, anti-biotic agent, anti-fungal agent), an anti-inflammatory agent, and/or an immunomodulatory agent. The therapeutic agent can be administered simultaneously with the particles and/or can be administered at a different time point. The route of administration of the therapeutic agent can be the same or different as the route of administration of the particles.

To treat a disorder of this invention, a composition comprising the particles of this invention may be administered to the subject in need thereof in an amount and for a time sufficient to induce a sustained improvement in at least one indicator that reflects the severity of the disorder. For example, the particles can be administered about every 1, 2, 3, 4, 5, 6, 7, 8, 9, or 10 or more days and/or weeks. In other embodiments, the particles can be about 1, 2, 3, 4, 5, 6, 7, 8, 9 or 10 or more times a week and/or month and/or year. In some embodiments, an improvement is considered "sustained" if the subject exhibits the improvement on at least two occasions separated by at least one to seven days, or in some instances one to six weeks. The appropriate interval will depend to some extent on what disease condition is being treated. It is within the purview of those skilled in the art to determine the appropriate interval for determining whether the improvement is sustained.

Kits that include particles of this invention and/or a pharmaceutical composition as described herein are also provided herein. Some kits include particles and/or compositions in a container (e.g., vial or ampule), and may also include instructions for use of the particles and/or composition in the various methods disclosed above. The particles and/or composition can be in various forms, including, for instance, as part of a solution or as a solid (e.g., lyophilized powder). The instructions may include a description of how to prepare (e.g., dissolve or resuspend) the particles in an appropriate fluid and/or how to administer the particles for the treatment of the diseases and disorders described herein.

The kits may also include various other components, such as buffers, salts, complexing metal ions and other agents described above in the section on pharmaceutical compositions. These components may be included with the chimeric protein or may be in separate containers. The kits may also include other therapeutic agents for administration with the chimeric protein. Examples of such agents include, but are not limited to, agents to treat the disorders or conditions described above.

The following examples are provided solely to illustrate certain aspects of the particles and compositions that are provided herein and thus should not be construed to limit the scope of the claimed invention.

EXAMPLES

The following EXAMPLES provide illustrative embodiments. Certain aspects of the following EXAMPLES are disclosed in terms of techniques and procedures found or contemplated by the present inventors to work well in the practice of the embodiments. In light of the present disclosure and the general level of skill in the art, those of skill will appreciate that the following EXAMPLES are intended to be exemplary only and that numerous changes, modifications, and alterations can be employed without departing from the scope of the presently claimed subject matter.

Example 1

Spatial-Temporal Delivery of IX40 Agonist and PD1 Inhibitor Using Nanoparticles Improves Therapeutic Efficacy of Cancer Immunotherapy Background. Cancer immunotherapy is an exciting new approach to cancer treatment and there is strong interest in strategies to improve the long-term durable response rates of cancer immunotherapy. One approach is to combine checkpoint inhibitors such as a PD-1 with T cell activator such as OX40 agonist to further increase immune activation. We conducted studies to determine whether we can improve the therapeutic efficacy of this approach by temporally controlling the activation of OX40 and inhibition of PD-1 pathways. To accomplish this, we utilized nanoparticles that can deliver anti-OX40 and anti-PD1 antibodies simultaneously to T cells.

Methods. Agonist antibody (anti-OX40) and antagonist antibody (anti-PD1) were conjugated to PLGA-PEG nanoparticles (AANPs) with precise ratio control and quantified by ELISA. Their specific binding to the target proteins was shown in vitro by flow cytometry. The tumor inhibition efficiency was assessed on mice bearing different tumor models. Two tumors were inoculated subcutaneously (105 B16F10 cells) or on fourth mammary fat pad (105 4T1 cells) on both flanks of mice. One side of the tumor was irradiated once and AANPs were injected twice every 3 days. In vivo depletion experiments were conducted on C56B16 mice and CD11b/c mice. Different populations of T cells in tumor and spleen were analyzed by flow cytometry and by fluorescence IHC staining. T cell killing assay and interferon gamma (IFN-γ) ELISpot were studied. Co-localization was demonstrated with fluorescence labeled antibodies and the corresponding AANPs.

Results. AANPs showed a 30% cure rate, compared to 10% of free antibodies, 0% of anti-PD1 conjugated NPs, and 0% of anti-OX40 conjugated NPs in a B16F10 melanoma model. We then re-challenged the cured mice with 2×105 B16F10 cells and none of the mice developed another tumor. In a 4T1 breast cancer model, the survival rate on day 39 was 50% with AANPs treatment, compared to 22% in the mixture of anti-PD1 conjugated nanoparticles and anti-OX40 conjugated nanoparticles, and 0% of free antibodies. We demonstrated that AANPs led to a higher medium TCD8+/Treg ratio in tumors. The therapeutic effect was mediated by CD8+ T cells as elimination of these cells abrogated the therapeutic effects. In vitro studies confirmed that AANPs were able to improve T cell stimulation compared to free antibodies by increasing IFN-γ excretion (2×). We further confirmed co-localization of antibodies with AANPs on tumor infiltration T cells in vivo.

Conclusions. Our data demonstrated that spatial-temporal delivery of agonist and antagonist can improve T cell activation and cancer immunotherapy.

Example 2

Activation of T Cells Using Nanoparticles Conjugated with PD1 Inhibitor and OX40 Agonist Improves Cancer Immunotherapy Combination immunotherapy has recently emerged as a powerful cancer treatment strategy. Clinical data suggest that the most effective immunotherapy regimens combine therapeutics that work synergistically to improve T cell activation. A promising treatment approach utilizes antagonistic antibodies to block checkpoint inhibitor receptors (aPD1) and agonistic antibodies to activate co-stimulatory receptors (aOX40) that are present on the surface of T cells. When these immunotherapeutic engage their respective immunomodulatory receptors simultaneously, they act synergistically to enhance T cell activation. Administration of these therapeutics as free antibodies can result in a suboptimal T cell binding events, with only a subset of the T cells binding both aPD-1 and aOX40 simultaneously (FIG. 1A). Here we show that the efficacy of combination immunotherapy is enhanced by spatiotemporal co-delivery of PD1 and OX40 using nanoparticles. We found that dual immunotherapy nanoparticles (DINPs) elicited higher rates of T cell activation in vitro than cultures receiving free PD1 and OX40 antibodies. Importantly, we found that administration of combination immunotherapy by DINPs significantly improves treatment efficacy in vivo by promoting effector T cell expansion. Our work demonstrates that nanotechnology can improve the therapeutic efficacy of combination immunotherapy by promoting simultaneous co-delivery of immunotherapeutic antibodies.

We conducted experiments to determine whether optimal T cell activation occurs when aPD-1 and aOX40 bind to their respective immunomodulatory receptors simultaneously (FIG. 1A). To conduct these studies, we developed DINPs capable of simultaneously co-delivering aOX40 and aPD-1 to immune cells.

Figure 5:
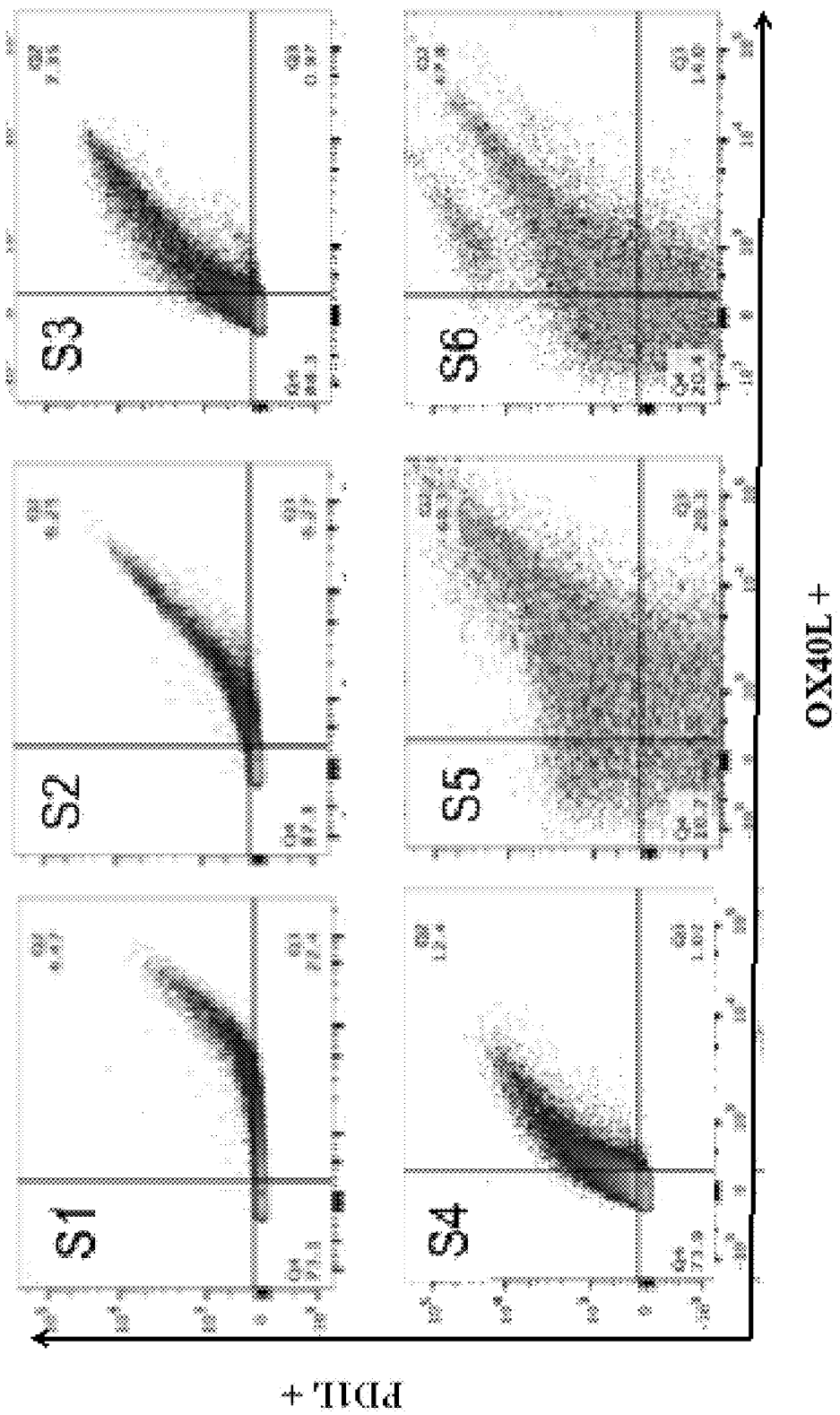
FIG. 5: Flow cytometric plots illustrating the ligand-binding of DINPs fabricated using different antibody conjugation chemistries reported in Table 1.

DINPs were formulated by conjugating aPD1 and aOX40 to maleimide-terminated poly(ethylene glycol)-b-poly(lactide-co-glycolide) (PEG-PLGA) nanoparticles using thiol-maleimide chemistry at a 1:1 ratio (Table 1). The change in size and zeta potential of nanoparticles (NPs) following fabrication provided preliminary evidence of successful dual antibody coating (FIGS. 1B-1F). To confirm that the aPD1 and aOX40 antibodies conjugating our DINPs are properly oriented and capable of this binding their respective ligands in a specific manner, we incubated our nanoparticle formulations with fluorescence labeled PD1L and OX40L proteins in vitro and assessed their binding efficacy using flow cytometric analysis. We found that anti-OX40-conjugated NPs (aOX40-NP) and anti-PD1-conjugated NPs (aPD1-NP) discretely bound to their corresponding ligands, while DINPs were able to bind both PD1L and OX40L simultaneously (FIG. 1G, FIG. 5).

Figure 2A:
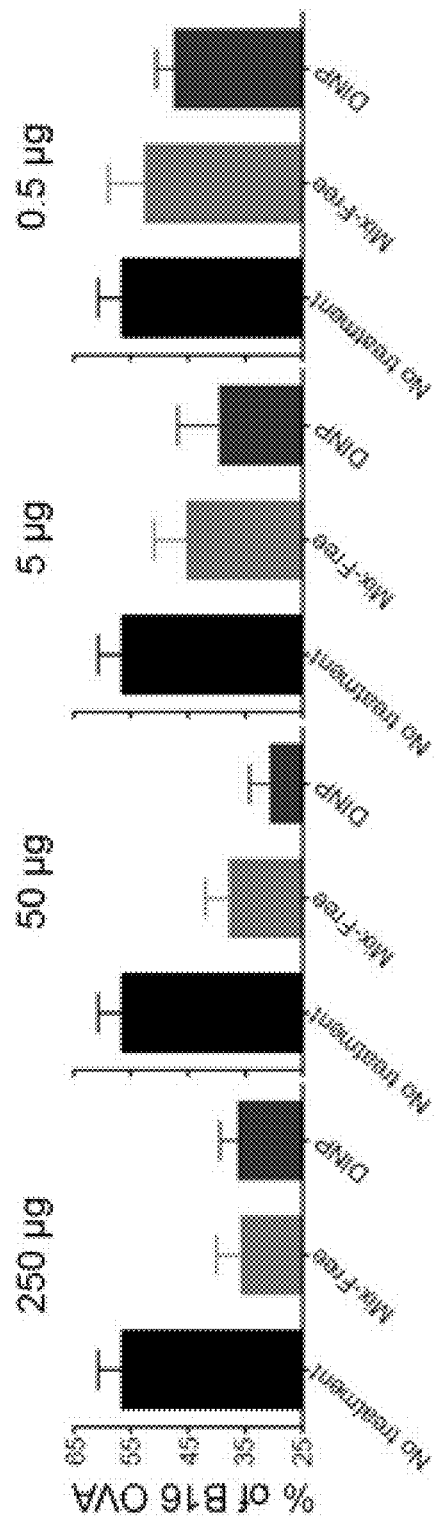
FIGS. 2A-C: DINPs facilitate CD8+ T cell activation and tumor cell killing in vitro. (2A) B16 ova viability is decreased following co-incubation with combination immunotherapy treated OT1 CD8+ T cells. (2B) Activation of OT1 CD8+ T cells is enhanced following combination immunotherapy treatment as assessed by ELISPOT. (C) and interferon gamma (INF-γ) production.
Figure 2B:
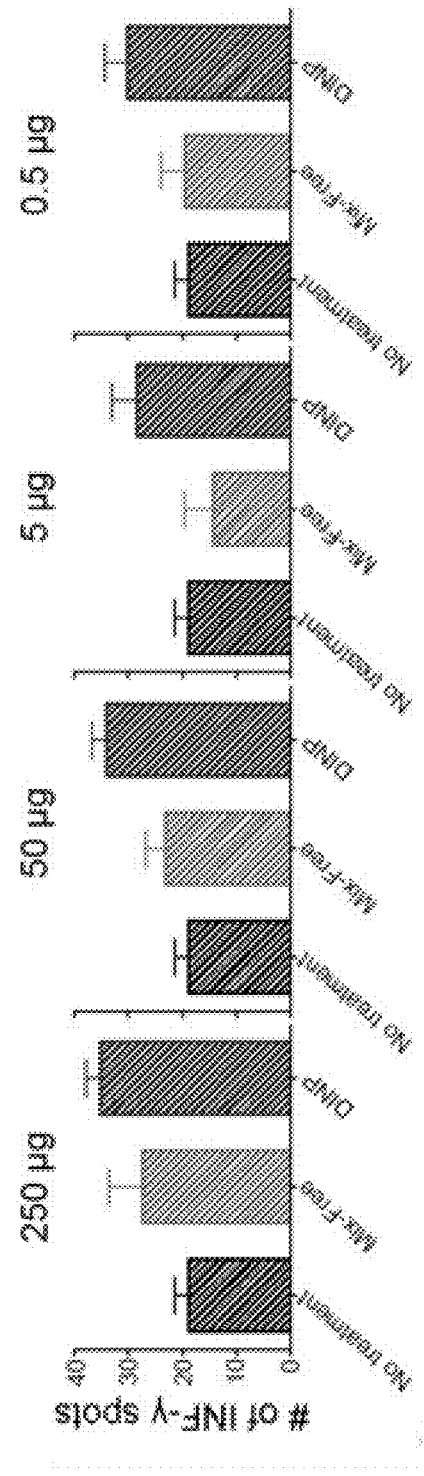
Figure 2C:
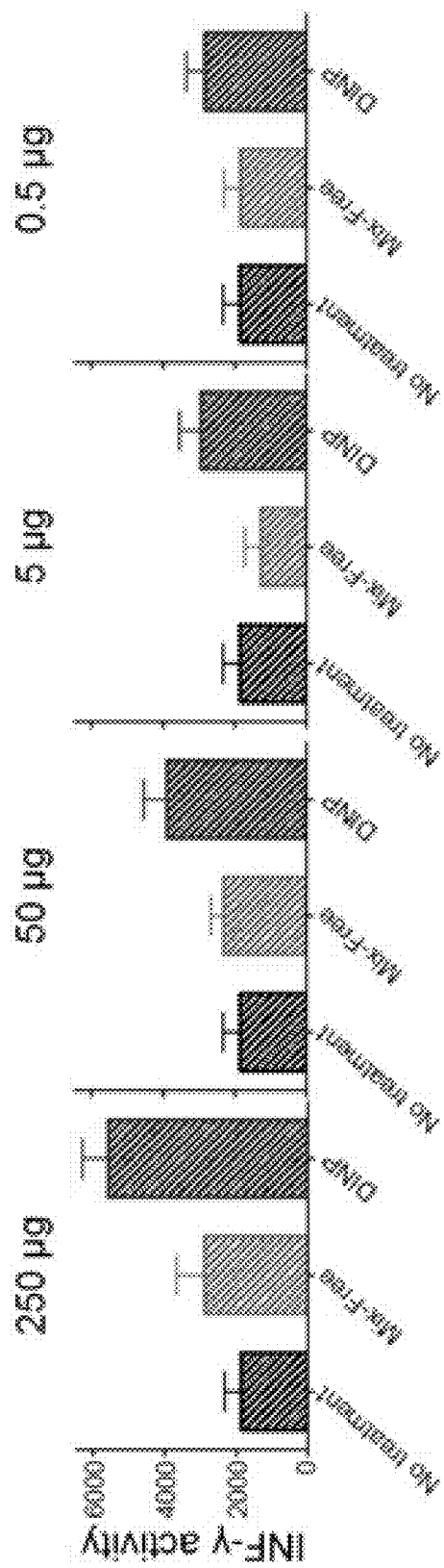

Next, we assessed the ability of DINPs to engage immunoregulatory receptors on T cells and elicit cell activation in vitro. OT1 CD8+ T cells were co-incubated with B16-ova tumor cells in media containing different concentrations of either DINPs or a mixture of free aPD1 and aOX40 antibodies. Following incubation, activation of T cells was determined by Enzyme-Linked ImmunoSpot (ELISPOT) and flow cytometric analysis. We found that DINP treated T cells demonstrated more robust activation and IFN-gamma production than cells treated with equivalent amounts of free antibody across all treatment concentrations (FIGS. 2B-2C). To assess whether DINP treated T cells demonstrated enhanced antitumor activity in vitro, we performed a cell-killing assay. Similar to our T cell activation assay, T cells were co-incubated with B16-ova tumor cells in media containing different concentrations of either DINPS or free aPD1 and OX40 antibodies for two days. Anti-tumor T cell activity was assessed by quantifying B16-ova cancer cell viability following co-incubation. We found that when compared to T cells treated with free antibodies, DINP treated T cells were generally more effective at killing tumor cells (FIG. 2A). These data suggest that simultaneous co-delivery of aPD1 and aOX40 using DINPs improves T cell activation.

Figure 3A:
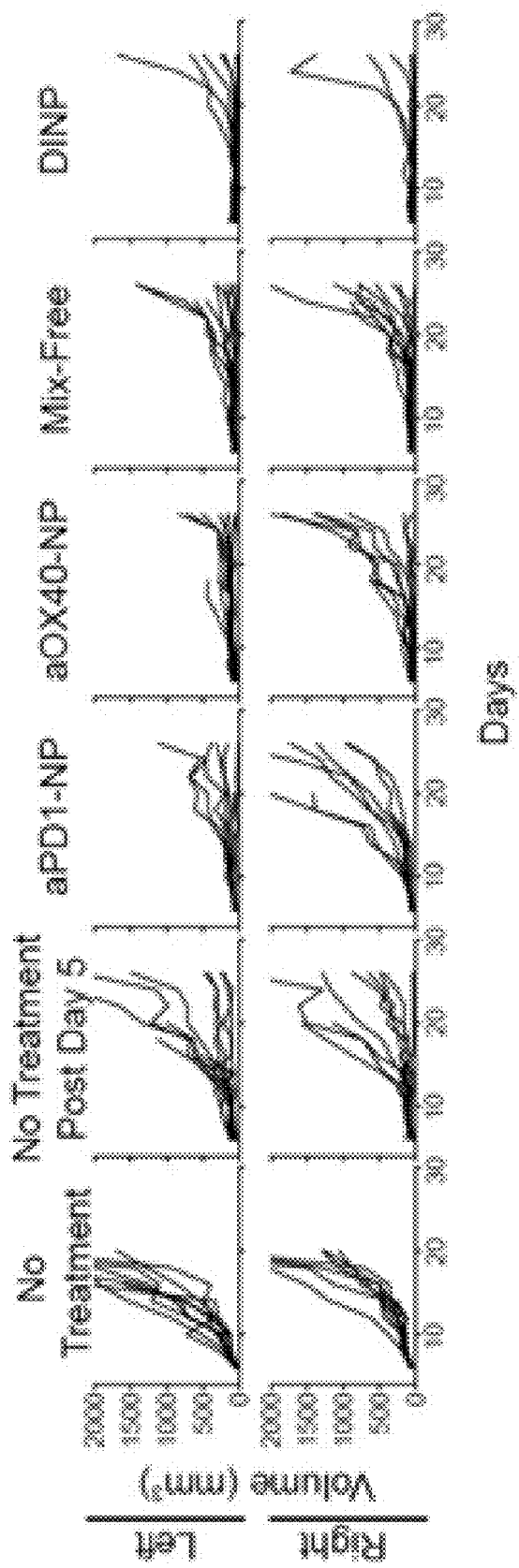
FIGS. 3A-G: DINPs improve the efficacy of combination immunotherapy in vivo. (3A) Individual tumor growth curves of B16F10 xenografts present in animals treated with nanoparticle mono-immunotherapy or combination immunotherapy administered as free antibodies or DINPs. (3B) Average tumor growth curves shown in (3A). (3C) Survival curves of animals in (3A). (3D) Survival curves of DINPs treated cured animals following tumor re-challenge. (3E) Individual growth curves of orthotopic 4T1 tumors present in animals treated with combination immunotherapy administered as free antibodies, a mixture of aOX40-NPs and aPD1-NPs, or DINPs. (3F) Average tumor growth curves shown in (3E). (3G) Survival curves of animals in (3E).
Figure 3B:
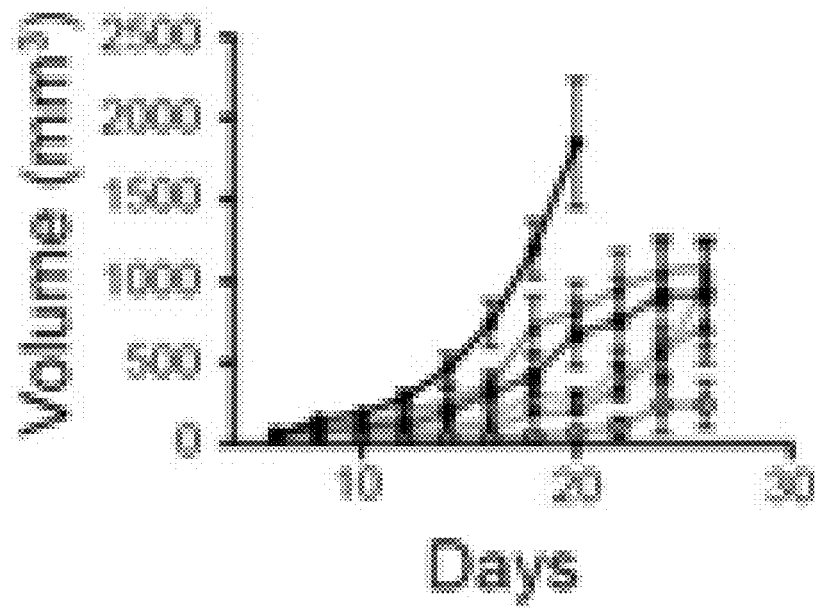
Figure 3C:
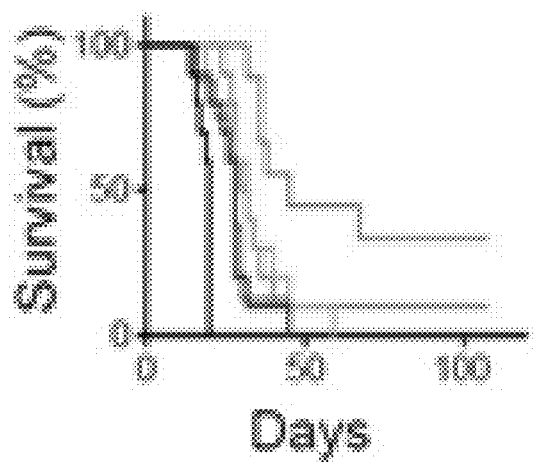
Figure 3D:
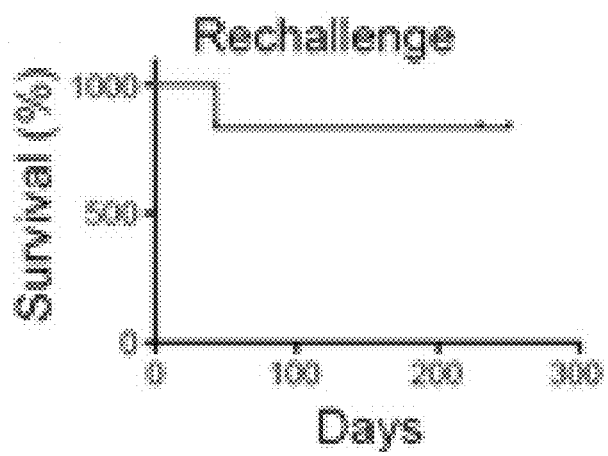
Figure 3E:
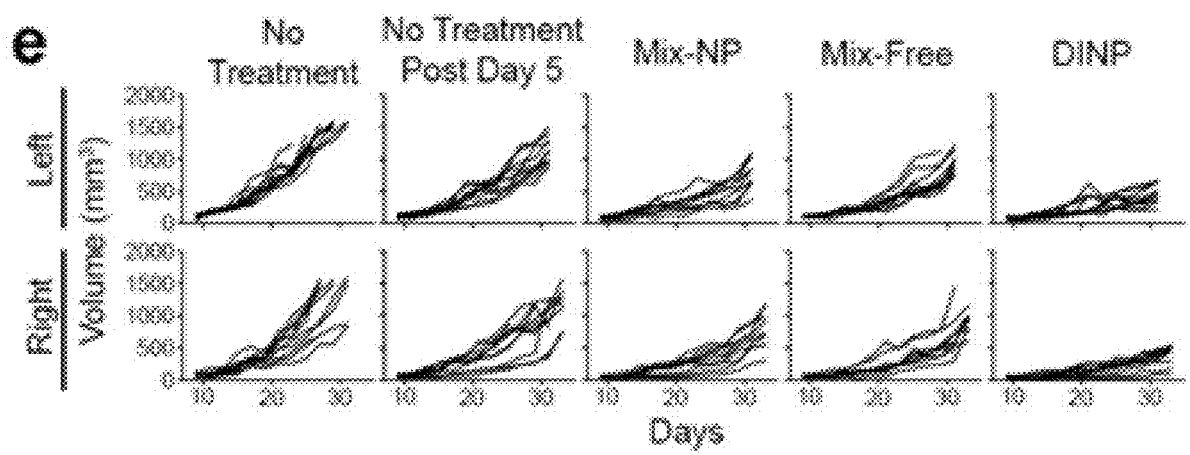
Figure 6:
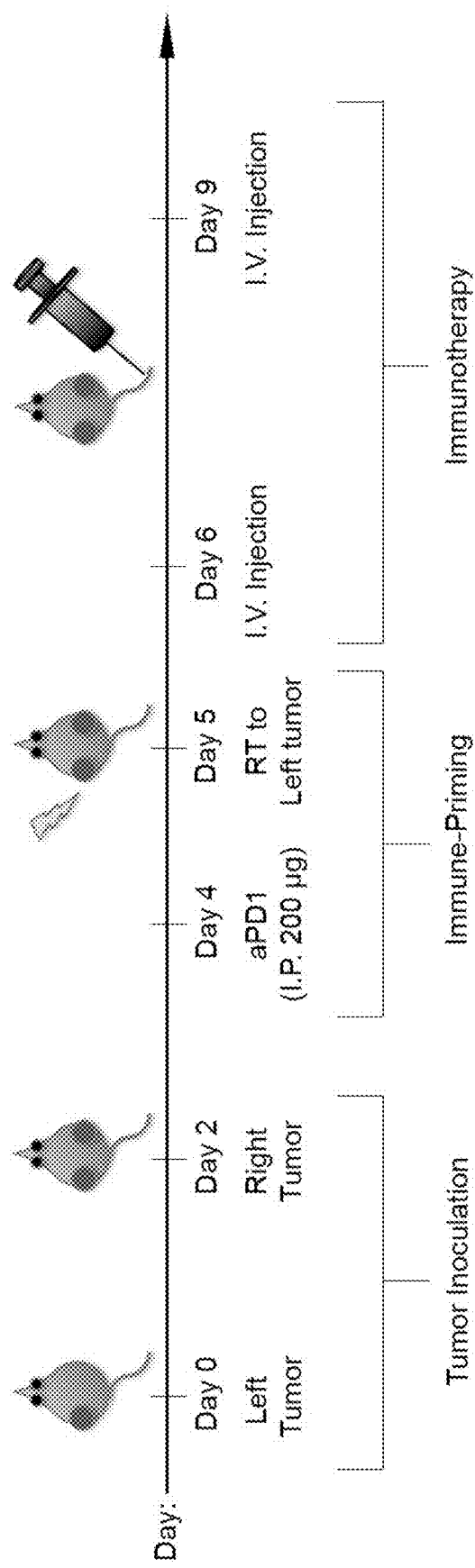
FIG. 6: Schematic depicting the treatment timelines for in vivo cancer immunotherapy experiments.
Figure 7A:
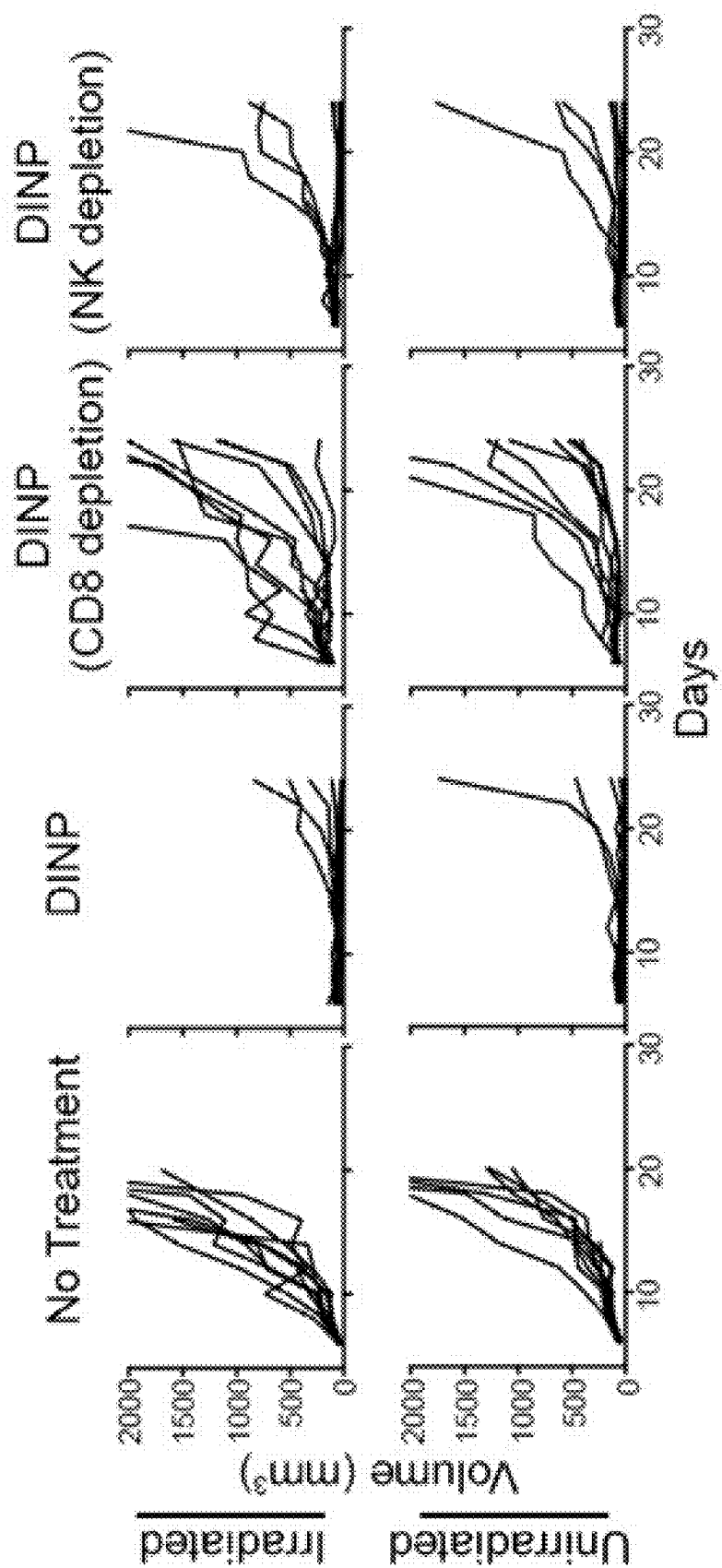
FIGS. 7A-C: DINPs facilitated enhancement of combination immunotherapy is lost following CD8+ T cell depletion. (7A) Individual growth curves of tumors in animals treated with DINPs combination immunotherapy with or without CD8+ T cell or NK cell depletion. (7B) Average tumor growth curves for each treatment arm shown in (7A). (7C) Survival curves of animals in (7A).
Figure 7B:
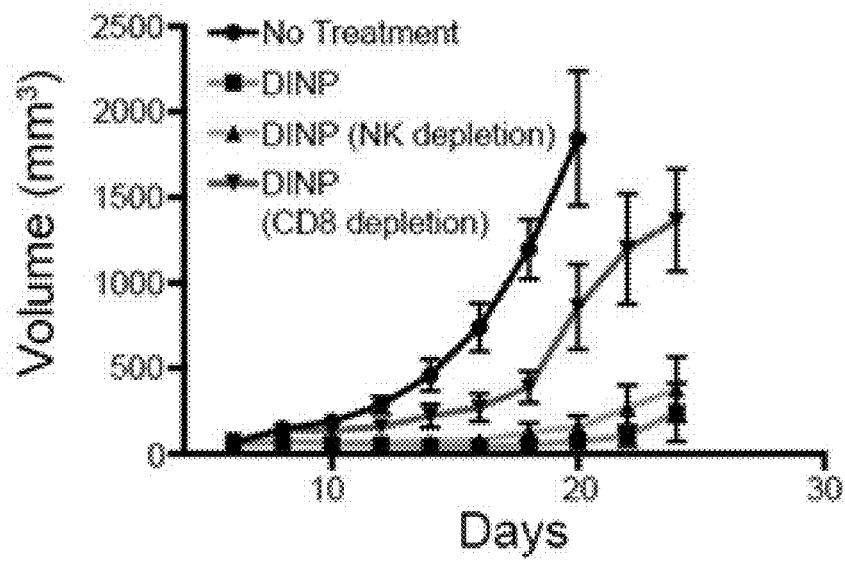
Figure 7C:
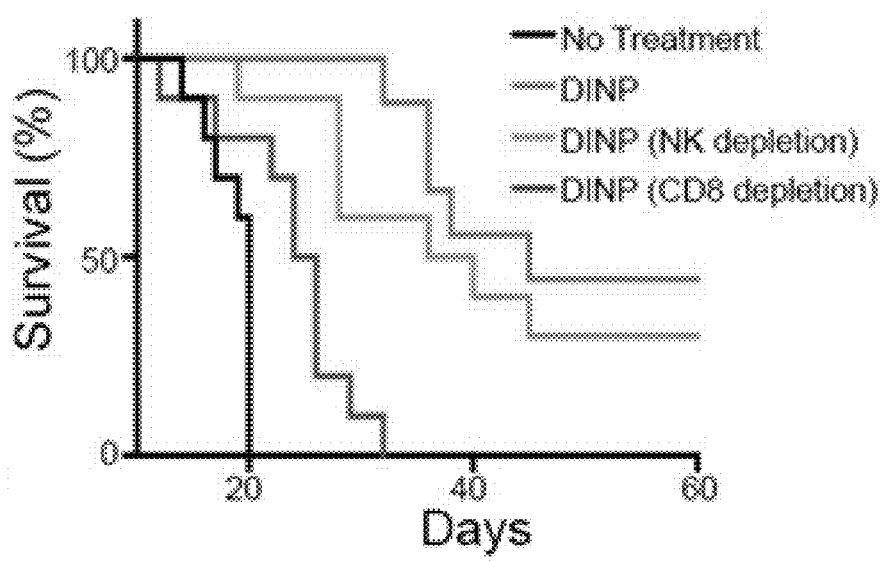

To investigate whether DINPs could improve combination immunotherapy in vivo, we treated animals bearing subcutaneous bilateral flank B16F10 melanoma xenografts with different immunotherapeutic regimens. Prior to treatment, animals were immune-primed with a single dose of PD1 and targeted radiotherapy to one flank tumor. Animals were then given OX40-NPs, PD1-NPs, DINPs, or a mixture of free aPD1 and aOX40 antibodies intravenously (FIG. 6). The immunotherapeutic efficacy of each treatment arm was assessed by measuring the growth rate of the un-irradiated tumor. We found that the animals treated with DINPs demonstrated the highest immunotherapeutic response rates across all treatment groups (FIGS. 3A-3C). Furthermore, the enhanced response observed in the DINP treatment arm is not attributable to nanoparticle-facilitated delivery of either aPD1 or aOX40 alone, as the aOX40-NP and aPD1-NP treatment arms did not provide a robust immunotherapeutic response (FIGS. 3A-3C). DINP combination immunotherapy yielded a cure rate of 30% (FIG. 3D). Importantly, 83% of cured mice successfully resisted tumor re-challenge, indicating that the treatment strategy is capable of inducing durable anti-tumor immunity (FIG. 3E). Moreover, DINP enhanced immunotherapeutic treatment efficacy is lost following CD8+ T cell depletion (FIG. 7A-7C).

Figure 3F:
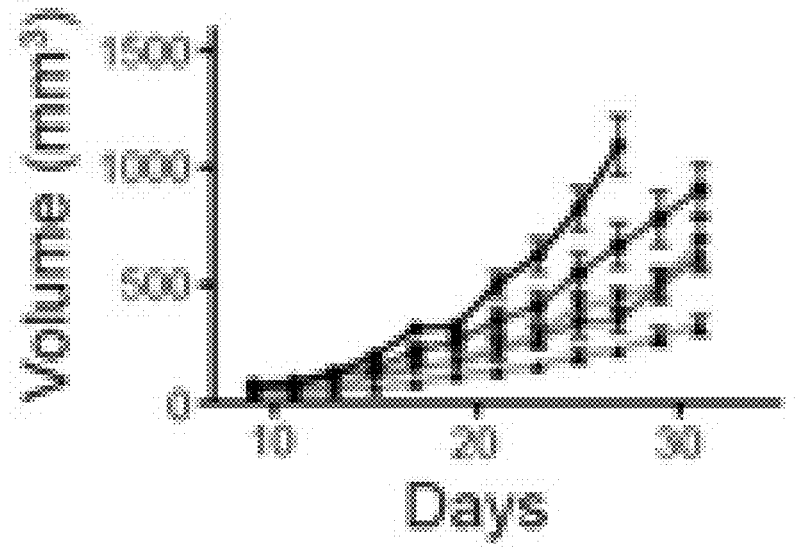
Figure 3G:
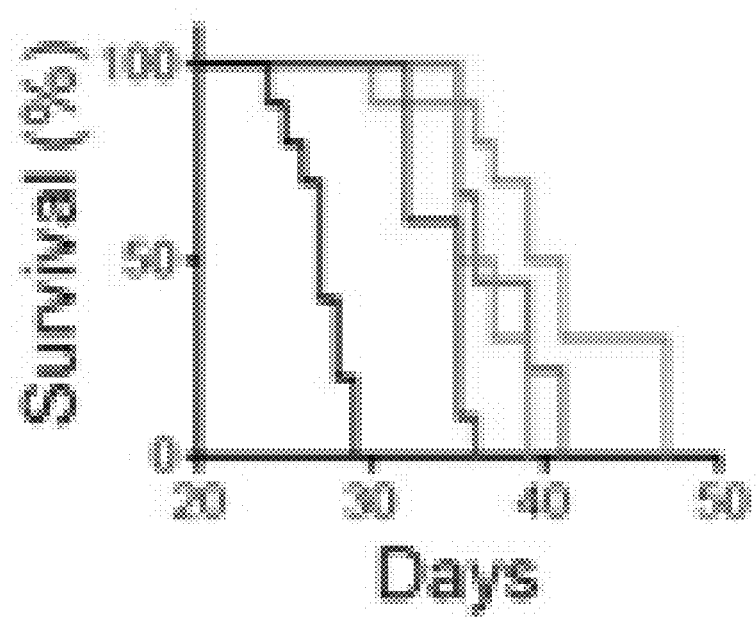

To further assess the efficacy of DINP combination immunotherapy, we repeated our in vivo study using an orthotopic model of breast cancer. Specifically, animals bearing bilateral orthotopic 4T1 tumors were immune-primed with aPD1 and radiotherapy and subsequently treated with different immunotherapeutic regimens (FIG. 6). As before, immunotherapeutic treatment efficacy was assessed by measuring the growth rate of the un-irradiated tumors. We found that animals receiving DINPs demonstrated the greatest treatment response across all treatment arms (FIGS. 3E-3G). Notably, we found that animals treated with a mixture of aPD1-NPs and aOX40-NPs demonstrated comparable treatment response to animals given a mixture of free aPD1 and aOX40 (FIGS. 3E-3G). This finding indicates that the enhanced immunotherapeutic response observed in our DINP treatment arm is not attributable to properties specific to nanoparticles, but rather due to simultaneous co-delivery of aPD1 and aOX40. Taken together, these data suggest that DINPs enhance combination immunotherapy by facilitating concurrent spatiotemporal co-delivery of immunotherapeutic antibodies to immune cells.

Figure 4A:
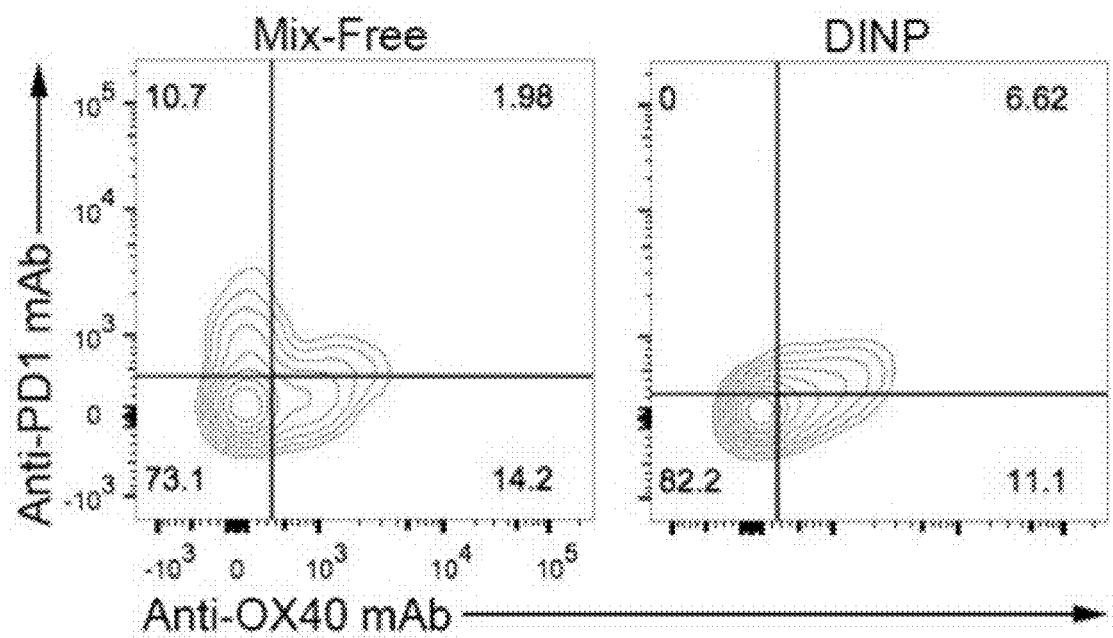
FIGS. 4A-D: DINPs improve the efficacy of combination immunotherapy in vivo by improving CD8+ T cell expansion and tumor infiltration. (4A) Flow cytometric analysis quantifying the number of T cells bound to fluorescently labeled aPD1 and aOX40 antibodies following combination immunotherapy administered in the form of free antibodies or DINPs in vivo. (4B) Ratio of T cells receiving both aPD1 and aOX40 therapy (Double Positive (DP)) to that receiving either of them (Single Positive (SP)) in animals treated with combination immunotherapy administered as free antibodies or DINPs. (4C) Flow cytometric analysis assessing the relative abundance of total tumor infiltration T cells, CD8+ T cells, and CD4+FOXP3+ regulatory T cells (Treg) subpopulations in un-irradiated tumors of animals undergoing different immunotherapy treatment regimens. (4D) Flow cytometric analysis assessing the relative abundance of effector memory CD8+ T cells and central memory CD8+ T cells in un-irradiated tumors.
Figure 4B:
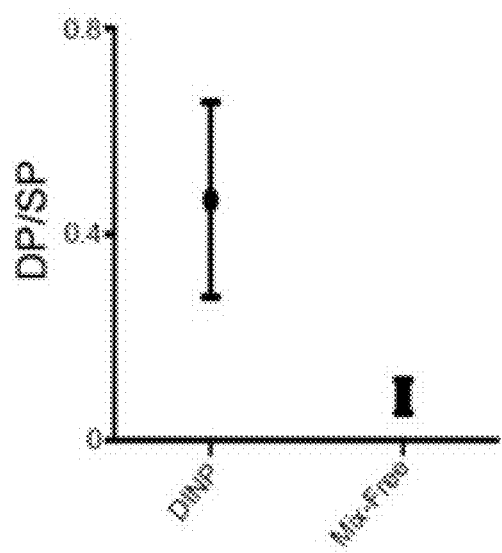
Figure 4C:
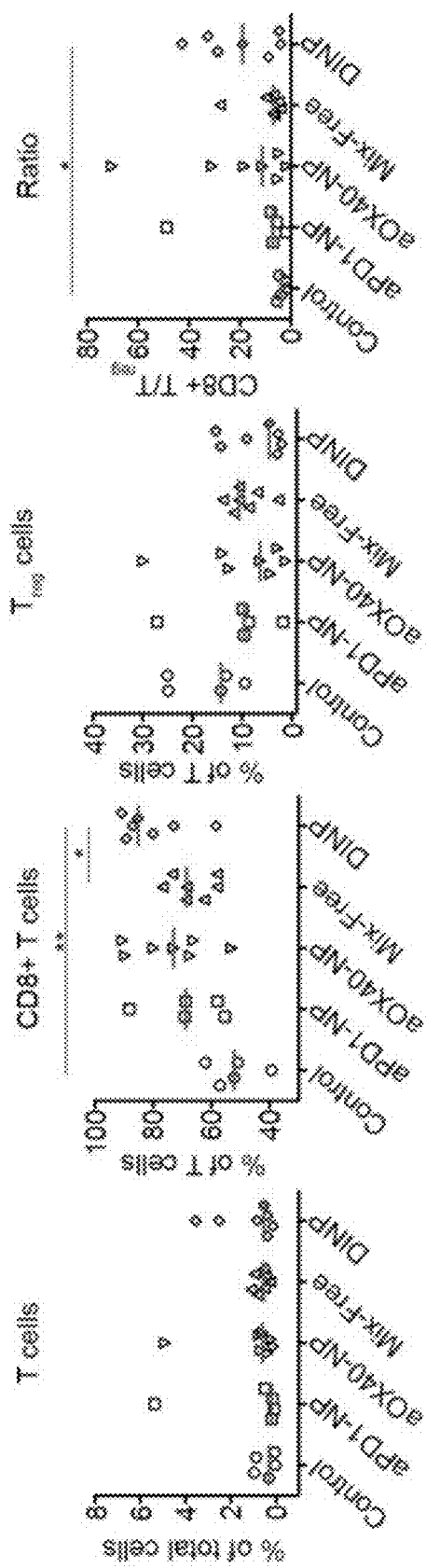
Figure 4D:
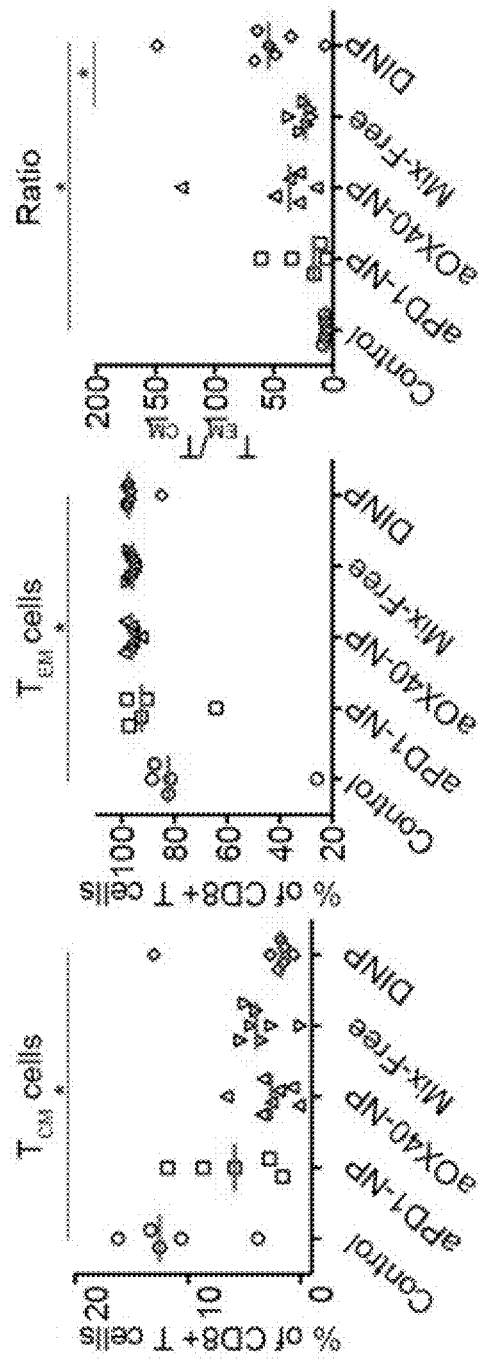
Figure 8A:
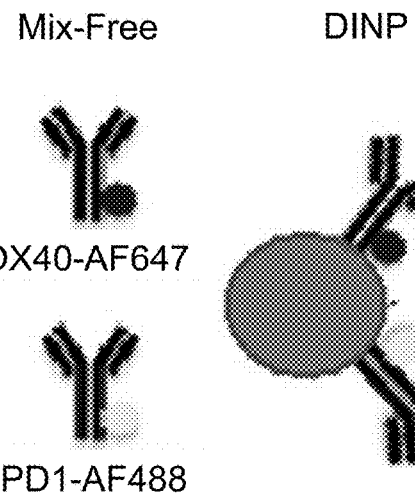
FIGS. 8A-B: Flow cytometric analysis allows for the assessment of immunotherapeutic antibody binding to T cells. (8A) T cell cultures were incubated with a mixture of florescent immunotherapeutic antibodies or fluorescently labeled DINPs in vitro. (8B) Flow plots quantitatively assessing the extent of T cell binding to aPD1 and aOX40.
Figure 8B:
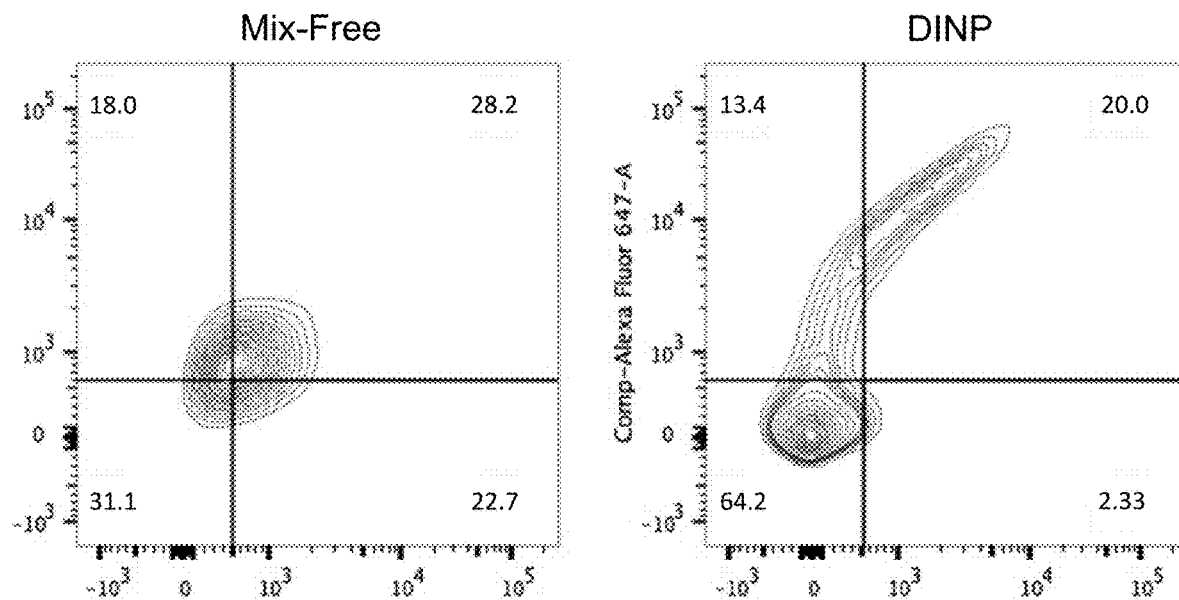
Figure 9:
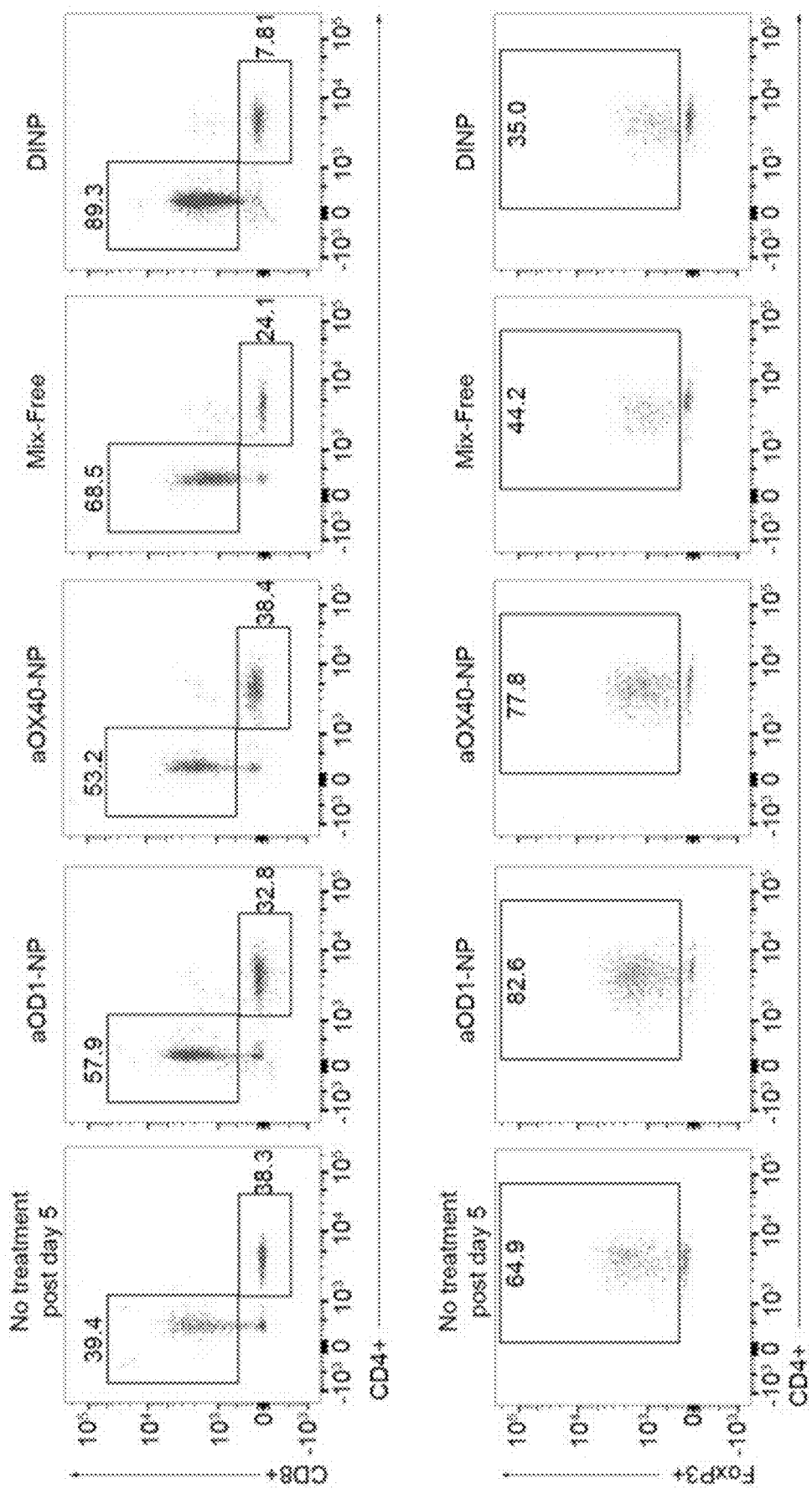
FIG. 9: Representative flow plots used to quantify the relative abundance of tumor infiltrating T cell subpopulations.
Figure 10A:
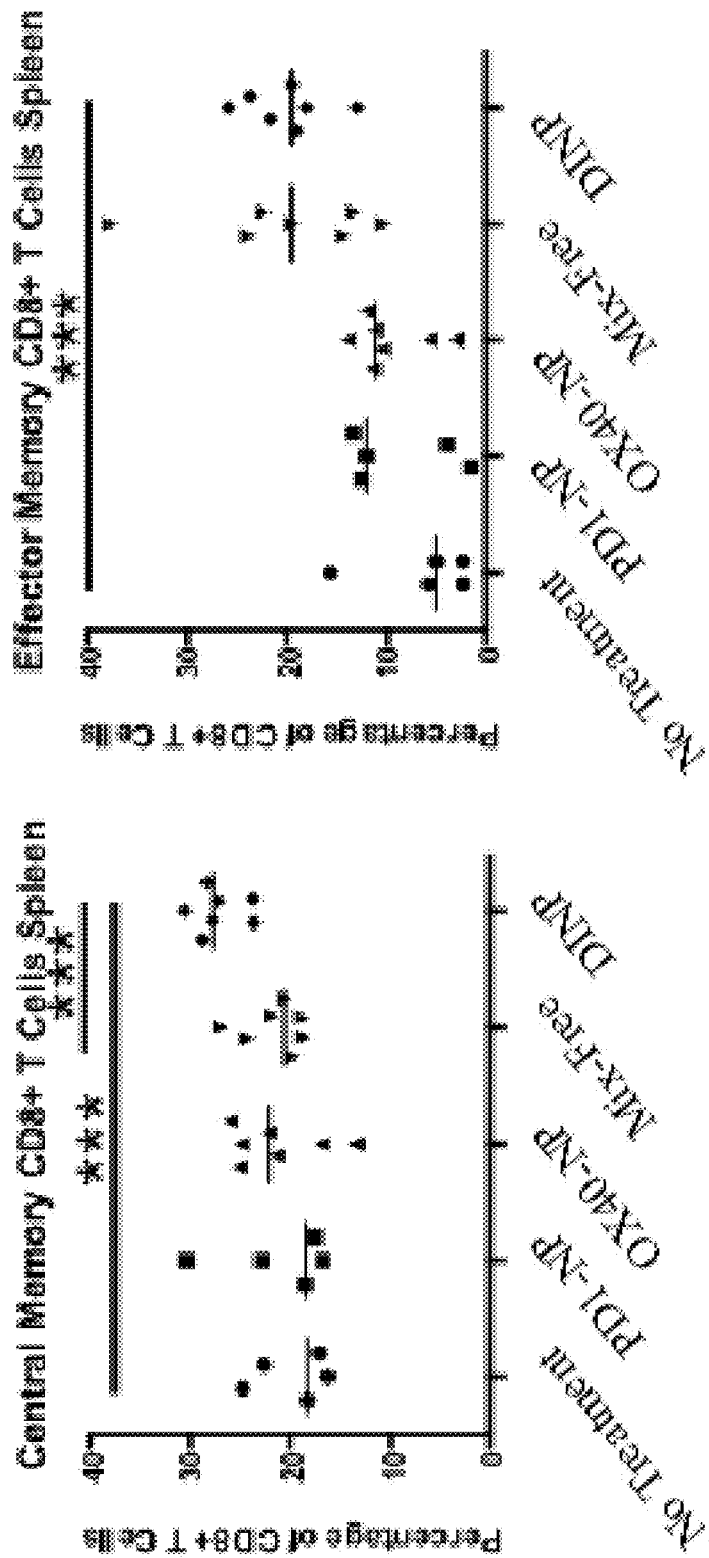
FIGS. 10A-B: DINP combination immunotherapy enhanced central memory T cell expansion (10A) and effector memory T cell expansion (10B).
Figure 10B:
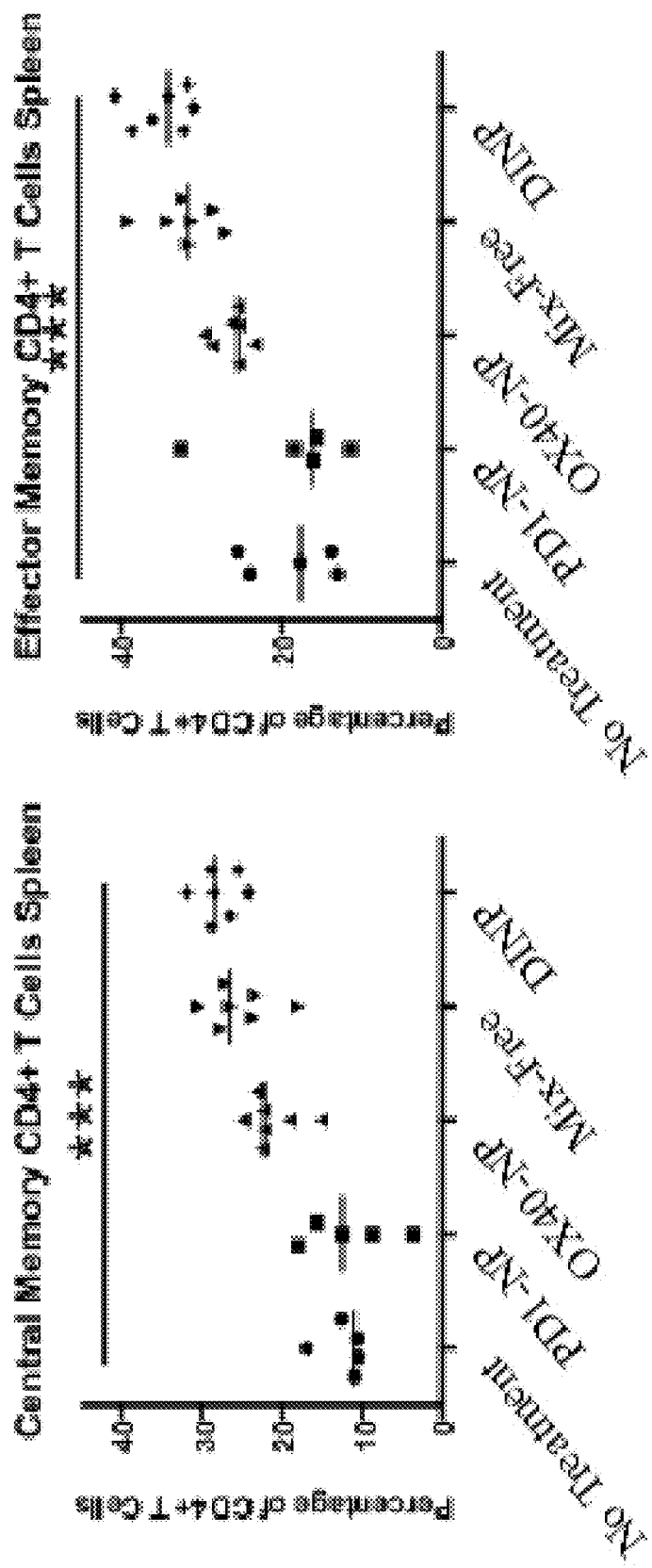
Figure 11A:
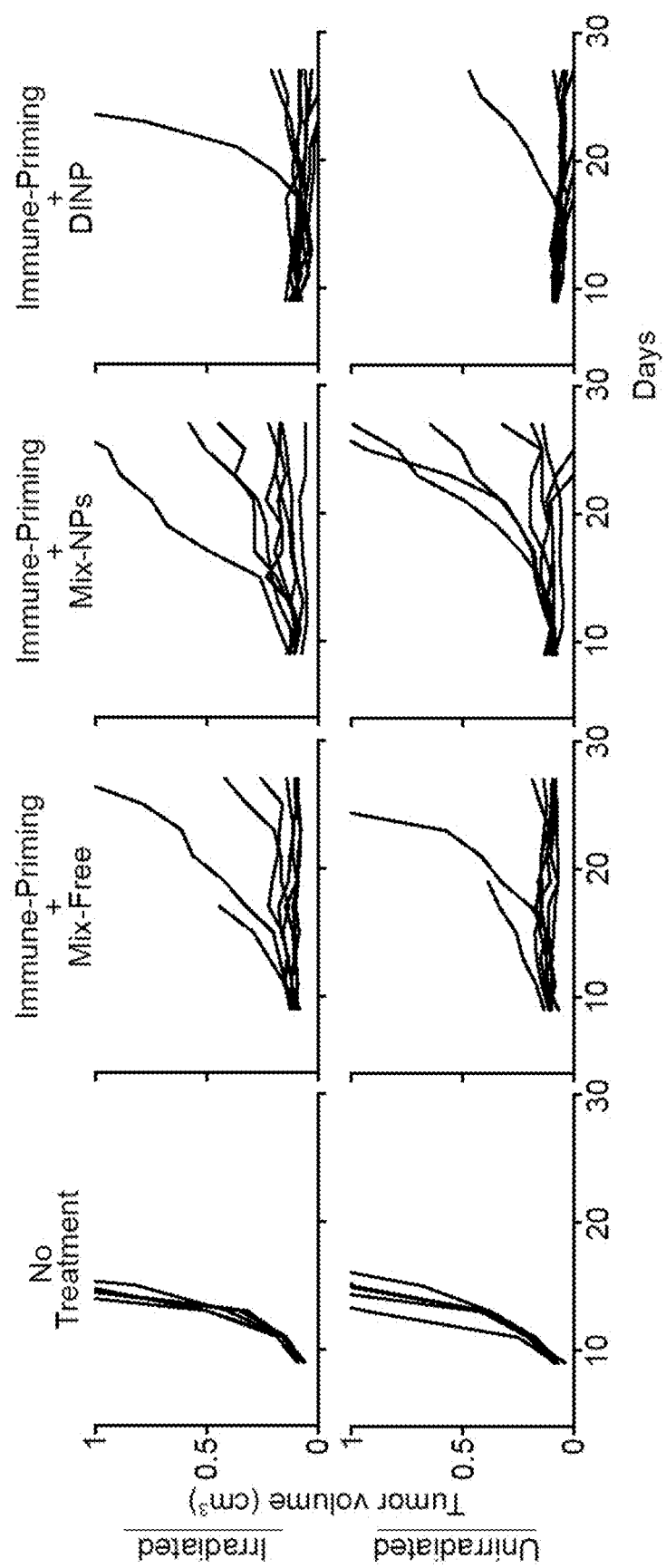
FIGS. 11A-B: DINP improves the efficacy of combination immunotherapy more efficiently than the mixture administrations in vivo. (11A) Individual tumor growth curves of B16F10 tumors present in animals treated with combination immunotherapy administered as a mixture of free antibodies, or a mixture of aOX40-NP plus aPD1-NP, or DINP (100 μg anti-PD1+100 μg anti-OX40 per dose, two doses in total). (11B) Average tumor growth curves and survival curves of animals shown in (11A). Tumor growth over time was compared by Mann-Whitney test. Data represents mean±standard error of the mean (SEM) (n=5 for no treatment group and n=8-10 for other groups). Differences in survival were determined for each group by the Kaplan-Meier method and the P value was calculated by the log-rank test. *P<0.05, **P<0.01.
Figure 11B:
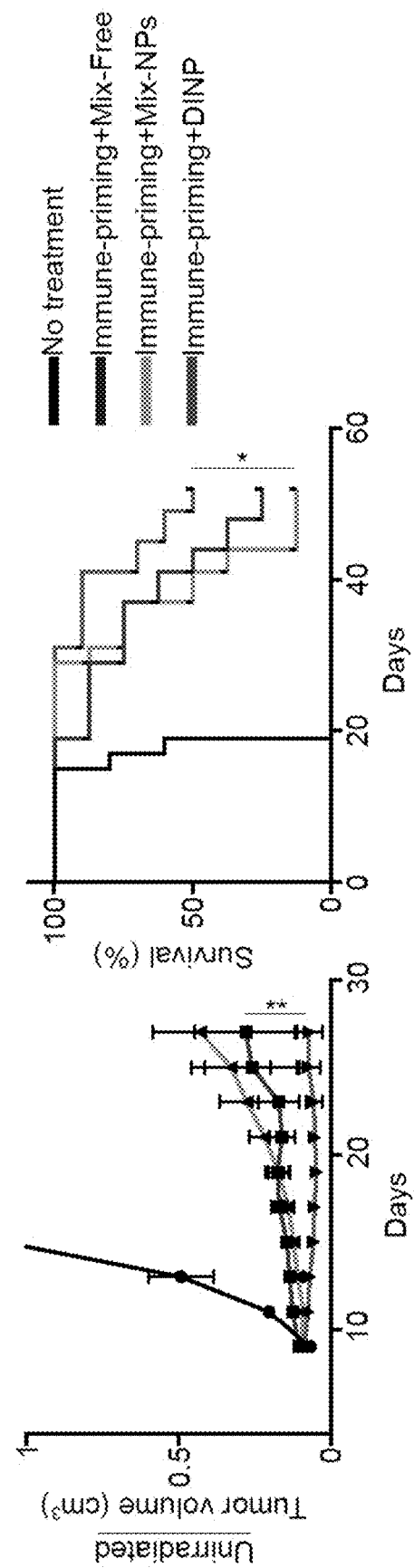

We next sought to determine the mechanism by which DINPs enhance antitumor immune response. First we confirmed that DINPs are capable of binding to immunoregulatory receptors on T cells in vivo. Specifically, we treated immune-primed animals bearing subcutaneous bilateral flank melanoma xenografts with fluorescence labeled free antibodies or DINPs intravenously. At three hours post administration, we assessed the extent to which aPD1 and aOX40 were bound to T cell populations using flow cytometric analysis (FIG. 8A-8B). We found that a greater number of T cells taken from animals treated with DINPs received concurrent aPD1 and aOX40 therapy (FIGS. 4A-4B). To determine if DINP facilitated co-delivery of aPD1 and aOX40 would translate to increased T cell activation and expansion in vivo, we quantified the number of tumor infiltrating T cells present in animals treated with various immunotherapeutic regimens using flow cytometric analysis. We found that animals treated with DINPs demonstrated an increased number of tumor infiltrating effector T cells when compared to animals receiving a mixture of free PD1 and aOX40 (FIG. 4C, FIG. 9). This finding was qualitatively supported by immunofluorescence images of tumors taken from animals undergoing different regimens. We also detected the subpopulation of effector memory and central memory in CD8+ T cells. The high percentage of effector memory CD8+ T cells as well as the high ratio of effector memory to central memory T cells after the treatment by DINPs indicated the high efficiency in stimulating naïve T cells into cytotoxic T cells (FIG. 4D). Furthermore, our data suggest that the DINP immunotherapy enhances treatment response by decreasing the prevalence of Tregs, an immunosuppressive cell type, within the tumor microenvironment as indicated by a reduced effector T cell/Treg cell ratio (FIG. 4C).

In summary, we demonstrate that concurrent spatiotemporal co-delivery of synergistic immunotherapeutics using nanoparticles can improve the treatment response of combination immunotherapy.

Materials. mPEG-PLGA (AK029; LA:GA=50:50 (w:w); MW: ~3000:36,000 Da), PLGA-PEG-Mal (Maleimide) (AI110; LA:GA=50:50; MW: 30,000-5,000 Da) were obtained from Polyscitech®. Anti-PD-1 (clone: RMP1-14), anti-OX-40 (CD134) (clone: OX-86), anti-CD8a (clone: 2.43), anti NK1.1 (clone: PK136) were obtained from BioXcell. Recombinant mouse PD-1, recombinant mouse OX40/TNFRSF4, and goat anti-human IgG (H+L) antibody were obtained from R&D Systems. Goat anti-rat IgG (H+L) secondary antibody HRP, Alexa Fluor® 488 (AF488) and Alexa Fluor® 647 (AF647) protein labeling kit, 1-Step™ ultra TMB-ELISA substrate solution, clear flat-bottom immuno 96-well plates were from ThermoFisher Scientific. All antibodies used for flow cytometric assays were from BD Biosciences and are listed in Table 2. All other chemicals were obtained from Sigma-Aldrich unless otherwise noted.

Cell lines. The B16-F10, B16-OVA and 4T1 cell lines were acquired from ATCC, where these lines were authenticated using morphology, karyotyping, and PCR based approaches and tested for mycoplasma. B16-F10 cells were cultured in Dulbecco's Modified Eagle's Medium (DMEM) (Gibco) supplemented with 10% fetal bovine serum (Mediatech), 100 U ml-1 penicillin and 100 µg ml-1 streptomycin (Mediatech), and 2 mM L-glutamine (Gibco). 4T1 cells were cultured in RPMI Medium 1640 (Gibco) supplemented with 10% fetal bovine serum (Mediatech), 100 U ml-1 penicillin and 100 µg ml-1 streptomycin (Mediatech), and 2 mM L-glutamine (Gibco). The cell cultures were maintained below 50% confluence and early-passage cultures (between 4 and 9) were utilized for experiments.

Preparation of simultaneous activation nanoparticles (DINPs). The DINPs were synthesized by a two-step method. First, PLGA-PEG-Mal nanoparticles were synthesized through nanoprecipitation technique. mPEG-PLGA and PLGA-PEG-Mal (7:3 weight ratio) were dissolved into acetone with a final polymer concentration of 10 mg/mL. The organic phase was added dropwise into the aqueous phase (endotoxin free $H_2O$) through a syringe under the oil to water ratio of 1:2. The solution was stirred at room temperature under a vacuum until the acetone completely evaporated. The solution were centrifuged and washed with endotoxin free $H_2O$. The PLGA-PEG-Mal NPs were then conjugated with PD1 and/or OX40 antibodies through maleimide-thiol click chemistry. Different feeding ratio of the antibodies (Table 1) were dissolved into EDTA (5 mM) containing PBS (pH=7.4) buffer and 0.75 µM tris(2-carboxyethyl)phosphine (TCEP) was added. The solution was gently shaken for 10 min at room temperature and PLGA-PEG-Mal NPs was added with a final NP concentration of 1 mg/mL. The reaction lasted for 4 h at room temperature or overnight at 4° C. with different incubation conditions (Table 1). The final product was centrifuged and washed with endotoxin free $H_2O$ or PBS and supernatant was collected.

Quantification of conjugated PD1 and/or OX40 antibodies on nanoparticles. The conjugated antibodies were quantified by calculating the difference from feeding amount and supernatant amount. The quantification of antibodies in the supernatant was analyzed by a standard sandwich ELISA assay. Specially, immuno 96-well plates were coated with 2 µg/ml of goat anti-human IgG antibody, followed by the addition of 100 ng/ml recombinant mouse PD-1 chimera protein or recombinant mouse OX40/TNFRSF4 Fc chimera protein, which were used as the capture agent for the bioactive anti-PD1 or anti-OX40 in the supernatant. 200 ng/ml of HRP-conjugated goat anti-rat IgG was then added as the detection antibody, followed by an HRP-sensitive colorimetric substrate.

Characterization of DINPs. Intensity-average diameter ($D_h$, also known as hydrodynamic diameter) and mean zeta potential (mean $\zeta$) of PLGA-PEG-Mal nanoparticles before (NPs) and after the conjugation of antibodies (DINPs) were analyzed by dynamic light scattering and an aqueous electrophoresis method using a Zetasizer Nano ZS Instrument (Malvern, Inc.). All measurements were based on the average of three separate measurements. The morphology of the nanoparticles was recorded by transmission electron microscopy (TEM, Zeiss EM 910).

Binding activity of DINPs. The recombinant mouse PD-1 chimera protein or recombinant mouse OX40/TNFRSF4 Fc chimera protein were first labeled by AF488 or AF647 protein labeling kit, respectively. Nanoparticles conjugated with anti-PD1 and/or anti-OX40 were blocked by 1% BSA PBS (pH=7.4) buffer for 1 hour. 200 µg NPs were incubated with 1 µg fluorescent PD-1 and/or OX40 proteins in PBS with 1% BSA for 2 hours. The solution was washed with washing buffer (PBS (pH=7.4) containing 0.05% Tween-20) 4 times. The binding between NPs and proteins were tested by flow cytometry.

Animal study. For all animal studies, eight-week-old female C57BL/6 mice (The Jackson Laboratory) were used. All animal work was approved and monitored by the University of North Carolina Animal Care and Use Committee.

Sample sizes were calculated based on our preliminary data. We calculated an effect size of 1.821. The nonparametric analog of this effect size can be stated in terms of $p_1$=Pr (X<Y), or an observation in Group X is less than an observation in Group Y when $H_1$ is true. The null hypothesis being tested is $p_1$=0.5. For effect size 1.821, $p_1$=0.099. A sample size of at least 8 in each group will have 80% power to detect a probability of 0.099 that an observation in Group X is less than an observation in Group Y, using a Wilcoxon (Mann-Whitney) rank-sum test, with a 0.05 two-sided significance level. Mice were assigned to treatment groups based on cage numbers.

Two perpendicular diameters were measured with a caliper and tumor volumes were calculated using the formula V=0.52×a×b^2, where a and b are the larger and smaller diameters, respectively. The tumor volumes were assessed every 2 days. Two independent researchers assessed tumor volume over time with one researcher blinded to the treatment group assignments. Statistical differences in average tumor growth curves were determined by two-way ANOVA using variables of time and volume. Differences in survival in each group were determined using the Kaplan-Meier method and the overall P value was calculated by the log-rank test using the GraphPad Prism 5.0. P value: *, P<0.05; , P<0.01; *, P<0.005.

Efficacy of DINPs in improving tumor immunotherapy. In the melanoma tumor model, 75,000 B16-F10 cells were suspended in DMEM, mixed with an equal volume of Matrigel (BD Biosciences), and subcutaneously injected on the left flank of C57BL/6 mice on day 0 and the right flank on day 2. 200-µg αPD-1 was intraperitoneally injected into animals on day 4. The left flank tumors were irradiated with 10 Gy on day 5 using a X-RAD 320. A lead shield protected the rest of the animal. DINPs, the mixture of antibodies and other control NPs (100 µg anti-PD1 and/or 100 µg anti-OX40 in 200 µL PBS) were injected intravenously on day 6 and 9. For the survival mice, at 1 or 2 month post-primary inoculation, secondary challenge of 200,000 B16-F10 cells was inoculated into the right flank and monitored without additional therapy. In the breast tumor model, 100,000 4T1 cells were suspended in RPMI Medium 1640, mixed with an equal volume of Matrigel (BD Biosciences), and injected on the left fourth mammary fat pad of BALB/c mice on day 0 and the right fourth mammary fat pad on day 2. The other steps were kept the same. In the depletion study, mice were treated by DINPs with the same procedure. 400 µg/dose of anti-CD8a or anti-NK1.1 were injected intraperitoneally on day 10.

T cell phenotype analysis. In the study of T cell phenotype, 100,000 B16-F10 cells were suspended in DMEM, mixed with an equal volume of Matrigel (BD Biosciences), and subcutaneously injected on the left flank of C57BL/6 mice on day 0 and the right flank on day 1. 200-µg αPD-1 was intraperitoneally injected into animals on day 6. The left flank tumors were irradiated with 10 Gy on day 7 using a X-RAD 320. A lead shield protected the rest of the animal. DINPs, the mixture of antibodies and other control NPs (100 µg anti-PD1 and/or 100 µg anti-OX40 in 200 µL PBS) were injected intravenously on day 8 and 11. Mice were sacrificed on day 15. Tissues were homogenized using the GentleMACs Dissociator and the samples were passed through a 70 µM cell strainer, followed by homogenization by using a 5 mL syringe plunger. The samples were centrifuged for 7 minutes at 1200 RPM, 4° C., decanting the supernatant. Samples were washed and resuspended in cold DPBS and transferred onto a 96 well V-bottom plate. Cells were resuspended in FVS510 viability stain (1:1000 dilution in 200 µL DPBS) for 40 minutes on ice. Wells not receiving viability staining were resuspended in DPBS. Cells were washed twice in staining buffer (0.02% NaN3, 2% BSA in DPBS), resuspended in 100 µL Fc block (1:50 dilution in staining buffer), and incubated on ice for 15 minutes. Antibody master mix was added to samples at 100 µL per sample with final antibody concentrations of:

CD4 FITC (1:75)
FoxP3 PE (1:75)
CD44 PerCPCy5.5 (1:75)
CD62L BV421 (1:75)
CD3 APC (1:75)
CD8 APCH7 (1:75)

Cells were incubated on ice for 45 minutes and washed twice with staining buffer. Cells were fixed and permeabilized using 250 µL fix/perm buffer overnight or for 50 min. (eBioscience FoxP3 buffer set). The following morning, cells were stained in 100 uL FoxP3 PE ab diluted 1:75 in perm wash buffer for 45 minutes on ice, wash 2× with staining buffer, and read out on a BD LSRFortessa flow cytometer. FlowJo flow cytometry software Version 10 was used for analyses.

Fluorescence immunohistochemistry study. Mice were treated the same as in T cell phenotype analysis. Tissues were fixed in 10% formalin for 72 h and then transferred to 70% ethanol. The slides were deparaffinized, placed in 10% Hydrogen peroxide in methanol for 30 minutes, and then gently rinsed in DI water. Immunofluorescence analysis of CD4-CD3-CD8 was performed on paraffin specimens using Mouse CD4 (14-9766 eBioscience), CD3 (A0452 Dako), and CD8 (14-0808 eBioscience). Antigen retrieval was performed on tissue slides with a tris based buffer (pH 8.5) for 72 minutes at 100 degrees Celsius and blocked with a protein block for 20 minutes at room temperature. The slides were given a hydrogen peroxidase block for 8 minutes at room temperature and first incubated in the CD4 dilution (1:10) (using Discovery Ab Diluent, 760-108) for 4 hours at room temperature, followed by the secondary antibody incubation (Alexa Fluor 647, A21247, goat anti-rat IgG, 1:100, using Discovery Ab Diluent, 760-108) at room temperature for 44 minutes. The slides were then given an antibody denaturation step of 95 degrees Celsius incubation for 12 minutes.

Following the denaturation, the slides were given another hydrogen peroxidase block for the CD3 dual antibody. The slides were incubated in the CD3 dilution (1:200, using Discovery Ab Diluent, 760-108) at room temperature for 1 hour, followed by the secondary antibody (Alexa Fluor 555, A21429, goat anti-rabbit IgG, 1:100, using Discovery Ab Diluent, 760-108) at room temperature for 44 minutes.

The CD8 triple antibody was prepared by another hydrogen peroxidase block. The slides were then incubated in the CD8 dilution (1:100, using PSS Discovery Diluent, 760-212) at room temperature for 2 hours, followed by the secondary antibody (Alexa Fluor 488, A11006, goat anti-rat IgG, 1:100, using Discovery Ab Diluent, 760-108) at room temperature for 44 minutes.

The slides were gently rinsed and placed in Hoescht 33258 Invitrogen solution, 2 ug/ml dilution at room temperature for 7 minutes for DAPI staining. The slides were finally coverslipped using Prolong Gold Antifade reagent, P36934 from Life Technologies.

Co-localization of DINPs. In the study of co-localization, 100,000 B16-F10 cells were suspended in DMEM, mixed with an equal volume of Matrigel (BD Biosciences), and subcutaneously injected on the left flank of C57BL/6 mice on day 0 and the right flank on day 1. 200-μg αPD-1 was intraperitoneally injected into animals on day 9. The left flank tumors were irradiated with 10 Gy on day 10 using a X-RAD 320. A lead shield protected the rest of the animal. Antibodies were first labeled by AF488 or AF647 protein labeling kit and then conjugated to the NPs by the same procedure in preparation of DINPs. Fluorescence-labeled DINPs or the mixture of fluorescence-labeled antibodies (200 μg anti-PD1 and 100 μg anti-OX40 in 200 μL PBS) were injected intravenously on day 12. Mice were sacrificed 3 hours later. Tissues were homogenized using the GentleMACs Dissociator and the samples were passed through a 70 μM cell strainer, followed by homogenization by using a 5 mL syringe plunger. The samples were centrifuged for 7 minutes at 1200 RPM, 4° C., decanting the supernatant. Samples were washed and resuspended in cold DPBS and transferred onto a 96 well V-bottom plate. Cells were resuspended in FVS510 viability stain (1:1000 dilution in 200 μL DPBS) for 40 minutes on ice. Wells not receiving viability staining were resuspended in DPBS. Cells were washed twice in staining buffer (0.02% NaN3, 2% BSA in DPBS), resuspended in 100 μL Fc block (1:50 dilution in staining buffer), and incubated on ice for 15 minutes. Antibody master mix was added to samples at 100 μL per sample with final antibody concentrations of:

CD3e BV421 (1:100)
CD45 BV786 (1:100)

Cells were incubated on ice for 45 minutes and washed twice with staining buffer and read out on a BD LSRFortessa flow cytometer. FlowJo flow cytometry software Version 10 was used for analyses.

In vitro cytotoxicity assay. Viably frozen OT1 CD8+ T cells were thawed and recovered overnight. Cells were incubated for 6 days with 100 IU/mL recombinant murine IL-2, anti-CD3/28 stimulation beads according to manufacturer protocol (Miltenyi, 130-095-925), and 1 μg/mL recombinant murine PD-L1 protein (R&D systems, 1019-B7), with media and reagents changed out every 48 hours. On day 7, T cells were co-incubated with B16-ova tumor cells at a 0.25:1 effector to target ratio in 100 μL media for 48 hr, along with 250, 50, 5, 0.5, or 0 μg of anti-PD-1/anti-OX40 antibody or equivalent dose of antibody conjugated nanoparticle. After co-incubation, non-adherent cells were washed from the plate, and remaining cell viability was measured with a CellTiter-Glo Luminescence kit (Promega, G7570), according to manufacturer protocol.

In vitro ELISpot. Viably frozen OT1 CD8+ T cells were thawed and recovered overnight. Cells were incubated for 6 days with 100 IU/mL recombinant murine IL-2, anti-CD3/28 stimulation beads according to manufacturer protocol (Miltenyi, 130-095-925), and 1 μg/mL recombinant murine PD-L1 protein (R&D systems, 1019-B7), with media and reagents changed out every 48 hours. On day 7, T cells were co-incubated with B16-ova tumor cells at a 10:1 effector to target ratio in 100 μL media for 3-6 hr, along with 250, 50, 5, 0.5, or 0 μg of anti-PD-1/anti-OX40 antibody or equivalent dose of antibody conjugated nanoparticle. After co-incubation, non-adherent T cells were transferred onto an anti-IFN-γ coated ELISpot plate (BD, 551083) and incubated for 72 hr before read-out, according to manufacturer protocol.

Example 3

Dual Immunotherapy Nanoparticle Improves T-cell Activation and Cancer Immunotherapy Combination immunotherapy has recently emerged as a powerful cancer treatment strategy. A promising treatment approach utilizes co-administration of antagonistic antibodies to block checkpoint inhibitor receptors, such as anti-programmed cell death-1 (aPD1), alongside agonistic antibodies to activate co-stimulatory receptors, such as anti-tumor necrosis factor receptor superfamily member 4 (aOX40). Optimal T-cell activation is achieved when both immunomodulatory agents simultaneously engage T-cells and promote synergistic pro-activation signaling. However, standard administration of these therapeutics as free antibodies results in suboptimal T-cell binding events, with only a subset of the T-cells binding to both aPD1 and aOX40. Here, we show that precise spatiotemporal co-delivery of aPD1 and aOX40 using nanoparticle (NP) (dual immunotherapy nanoparticle, DINP) results in improved T-cell activation, enhanced therapeutic efficacy, and increased immunological memory. We demonstrate that DINP elicits higher rates of T-cell activation in vitro than free antibodies. Importantly, we demonstrate in two tumor models that combination immunotherapy administered in the form of DINP is more effective than the same regimen administered as free antibodies. Our work demonstrates a novel strategy to improve combination immunotherapy using nanotechnology.

Clinical data suggest that combination immunotherapy regimens that enhance T-cell activation are effective in treating metastatic disease. Currently, the most effective combination immunotherapeutic regimens consist of combining multiple antagonistic antibodies that target checkpoint inhibition receptors. However, some combination checkpoint blockade agents demonstrate significant autoimmune-mediated toxicity. Consequently, recent efforts have focused on combining immune checkpoint blockade agents with T-cell agonists, because these combination immunotherapy strategies elicit less immune-mediated toxicity in the clinical setting.

A particularly promising combination immunotherapeutic regimen is the co-administration of aPD1 and aOX40 to block T-cell inhibition and induce T-cell activation, respectively. With this strategy, maximum T-cell activation would be expected when the T-cells are able to bind both agents (aPD1 and aOX40) simultaneously. However, standard administration of these therapeutics as free antibodies results in only a subset of the T cells binding to both aPD1 and aOX40 (FIG. 1A). Moreover, it is likely that the T-cells bind to each agent sequentially rather than simultaneously. We conducted experiments to determine whether single binding events/sequential binding resulted in suboptimal T-cell activation, treatment efficacy, and immune memory formation when compared to simultaneous binding of both aPD1 and aOX40. We conducted experiments to determine whether we could increase the spatiotemporal precision of aOX40 and aPD1 co-delivery to T-cells using a dual-immunotherapy NP platform (DINP), thereby promoting simultaneous dual-therapeutic binding events.

DINP was formulated by conjugating aPD1 and aOX40 to maleimide-terminated poly(ethylene glycol)-b-poly(lactide-co-glycolide) (PEG-PLGA) NP using thiol-maleimide chemistry. We aimed to achieve 1:1 aPD1 to aOX40 ratio due to our lack of knowledge about the best ratio determined by several factors such as actual amount and distribution of PD1 and OX40 receptors on T cells. We also hypothesized that increased T cell activation would be associated with high density of binding sites per NP. We were able to achieve a sizeable number of binding sites per NP by incubation of 200 µg/mL aPD1 and 100 µg/mL aOX40 to 1 mg/mL NP, resulting in 49.1±5.5 µg of aPD1 and 44.0±6.0 µg of aOX40 conjugated to per mg NP (Table 1).

Figure 1B:
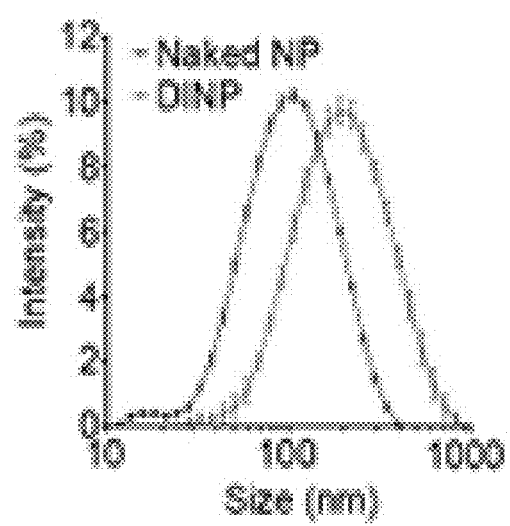
Figure 1C:
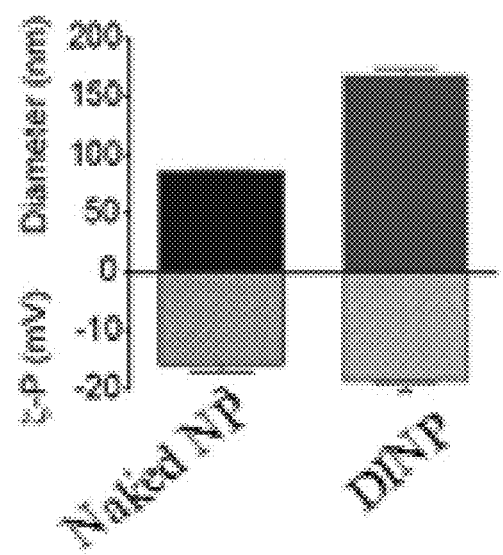
Figure 1G:
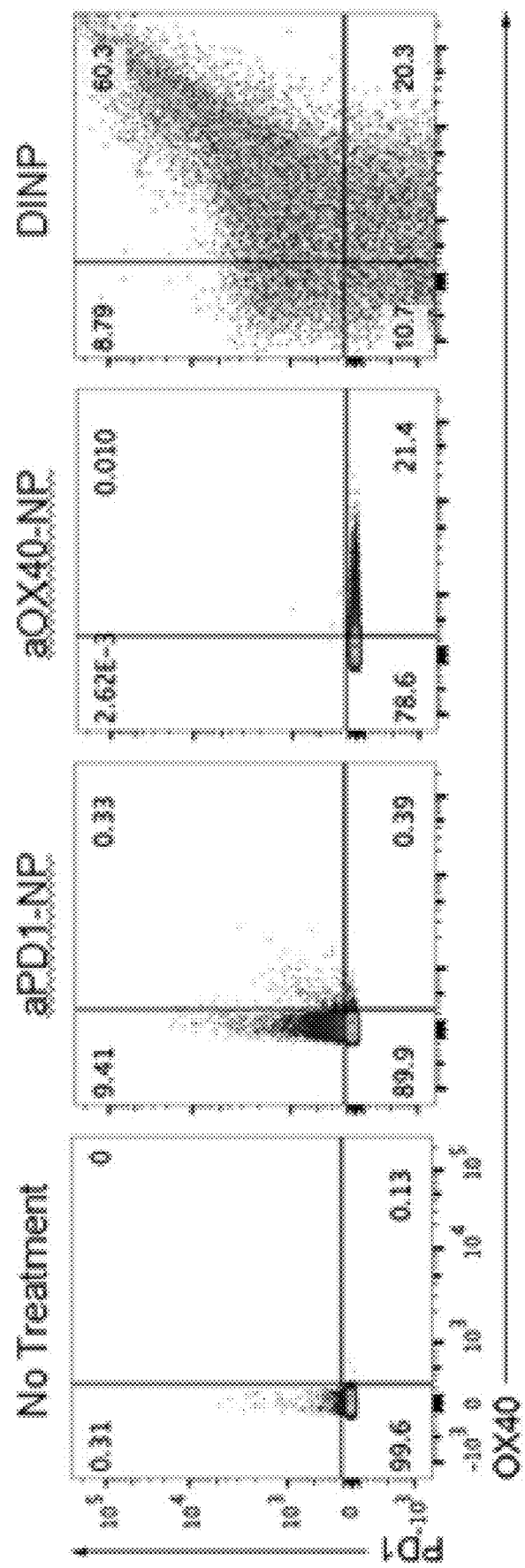

Physical characterization of DINP demonstrated a spherical morphology with an average hydrodynamic diameter of 166.9±6.5 nm and a negatively charged surface (FIGS. 1B-1C). As the hydrodynamic diameter of NP was affected by the surface bound species and electrical outer layer, we also measured DINP size using TEM images (FIGS. 1D-1F). The average size was 67.7±11.2 for naked NP and 100.1±18.4 for DINP, indicating almost a single layer of antibodies was conjugated to DINP. To confirm that at least some of the aPD1 and aOX40 antibodies were properly oriented and capable of binding to their respective ligands, we incubated DINP with fluorescently labeled recombinant murine PD1 or OX40 Fc chimeric proteins that bind aPD1 and aOX40 respectively. Using flow cytometry, we showed that aOX40-conjugated NP (aOX40-NP) and aPD1-conjugated NP (aPD1-NP) were able to bind to their corresponding proteins, while DINP was able to simultaneously bind to both proteins, confirming proper orientation (FIGS. 1G, 5).

Next, we assessed the ability of DINP to engage immunoregulatory receptors on T-cells and elicit activation in vitro. Antigen-expanded OT1 CD8+ T cells were cultured in conditions previously demonstrated to mimic exhaustion, then co-incubated with B16-OVA tumor cells in media containing different concentrations of DINP or a mixture of free aPD1 and aOX40 antibodies. Following incubation, T-cell activation was assessed by IFN-γ Enzyme-Linked ImmunoSpot (ELISpot)[10]. We found that DINP-treated T-cells demonstrated both greater number of IFN-γ producing cells and higher overall activity of IFN-γ production compared to cells treated with equivalent amounts of free antibodies across all treatment concentrations (FIGS. 2B-2C). To assess whether DINP-treated T-cells also demonstrated enhanced antitumor activity in vitro, we evaluated the killing of B16-OVA tumor cells by DINP-treated OT1 CD8+ T-cells. DINP-treated T-cells were significantly more effective at killing B16-OVA than T-cells treated with free antibodies (FIG. 2A). Our data suggest that DINP is more effective in inducing T-cell activation and cytotoxicity than conventional dual-antibody therapy in vitro.

To investigate whether DINP can improve combination immunotherapy in vivo, C57BL/6 mice bearing bilateral flank B16-F10 melanoma tumors were treated with various immunotherapy regimens. Since OX40 is exclusively expressed by activated T-cells[7, 11], mice were first immune-primed with a single dose of aPD1[12] (200 µg, intraperitoneally) and radiotherapy (10 Gy) to one of the flank tumors[13]. Animals were then given aOX40-NP, aPD1-NP, DINP, or a mixture of free aPD1 and aOX40 antibodies intravenously (FIG. 6). The therapeutic efficacy of each treatment arm was assessed by measuring the growth rate of non-irradiated tumors Animals treated with DINP demonstrated the highest immunotherapeutic response rates across all treatment groups with a cure rate of 30% (FIGS. 3A-3C, 11A-11B). Importantly, 5/6 of cured mice successfully resisted tumor re-challenge, indicating that the treatment strategy is capable of inducing durable anti-tumor immunological memory formation (FIG. 3D).

To validate our in vivo results, we evaluated the therapeutic efficacy of DINP treatment using an orthotopic 4T1 breast cancer model. Animals bearing bilateral mammary fat pad 4T1 tumors were immune-primed with aPD1 and radiotherapy and subsequently treated with different immunotherapeutic regimens. As seen in the B16-F10 model, we observed that DINP treatment resulted in the greatest control of tumor burden and increased the survival time of tumor-bearing animals by over 20% when compared to all other treatment arms (FIGS. 3E-G). Importantly, we found that DINP treatment was significantly more effective than the combination of aPD1-NP and aOX40-NP, demonstrating that the enhanced immunotherapeutic response observed in our DINP treatment arm cannot simply be attributable to properties specific to NP.

Figure 12A:
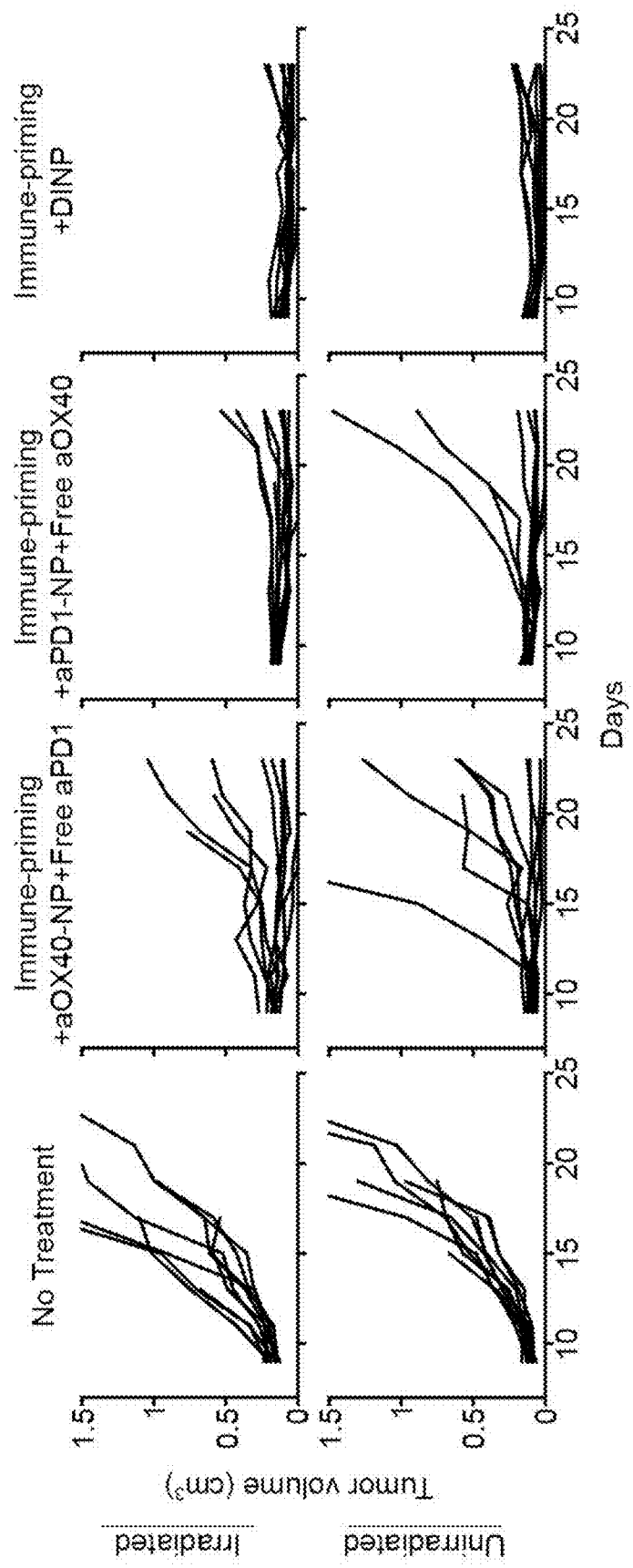
FIGS. 12A-B: DINP improves the efficacy of combination immunotherapy in vivo. (12A) Individual tumor growth curves of B16F10 tumors present in animals treated with aOX40-NP plus free aPD1, aPD1-NP plus free aOX40 or DINP (100 μg anti-PD1+100 μg anti-OX40 per dose, two doses in total). (12B) Average tumor growth curves and survival curves of animals shown in (12A). Tumor growth over time was compared by two-way ANOVA (P<0.0001) followed by Turkey's multiple comparison tests. Data represent mean±standard error of the mean (SEM) (n=10). Differences in survival were determined for each group by the Kaplan-Meier method and the P value between mixture of free antibodies and DINP was calculated by the log-rank test. *P<0.05, **P<0.01.
Figure 12B:
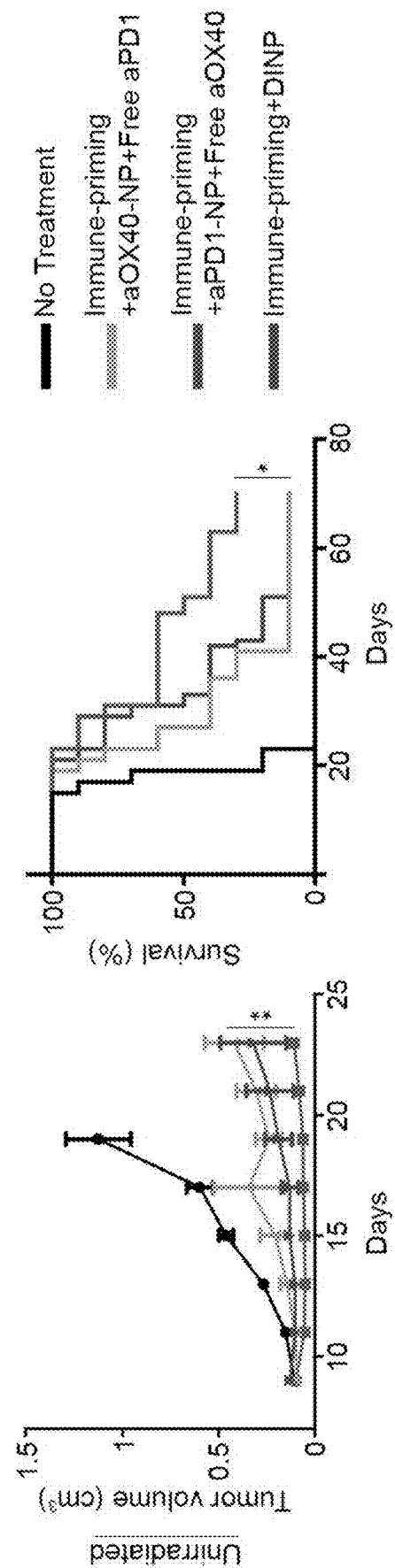
Figure 13A:
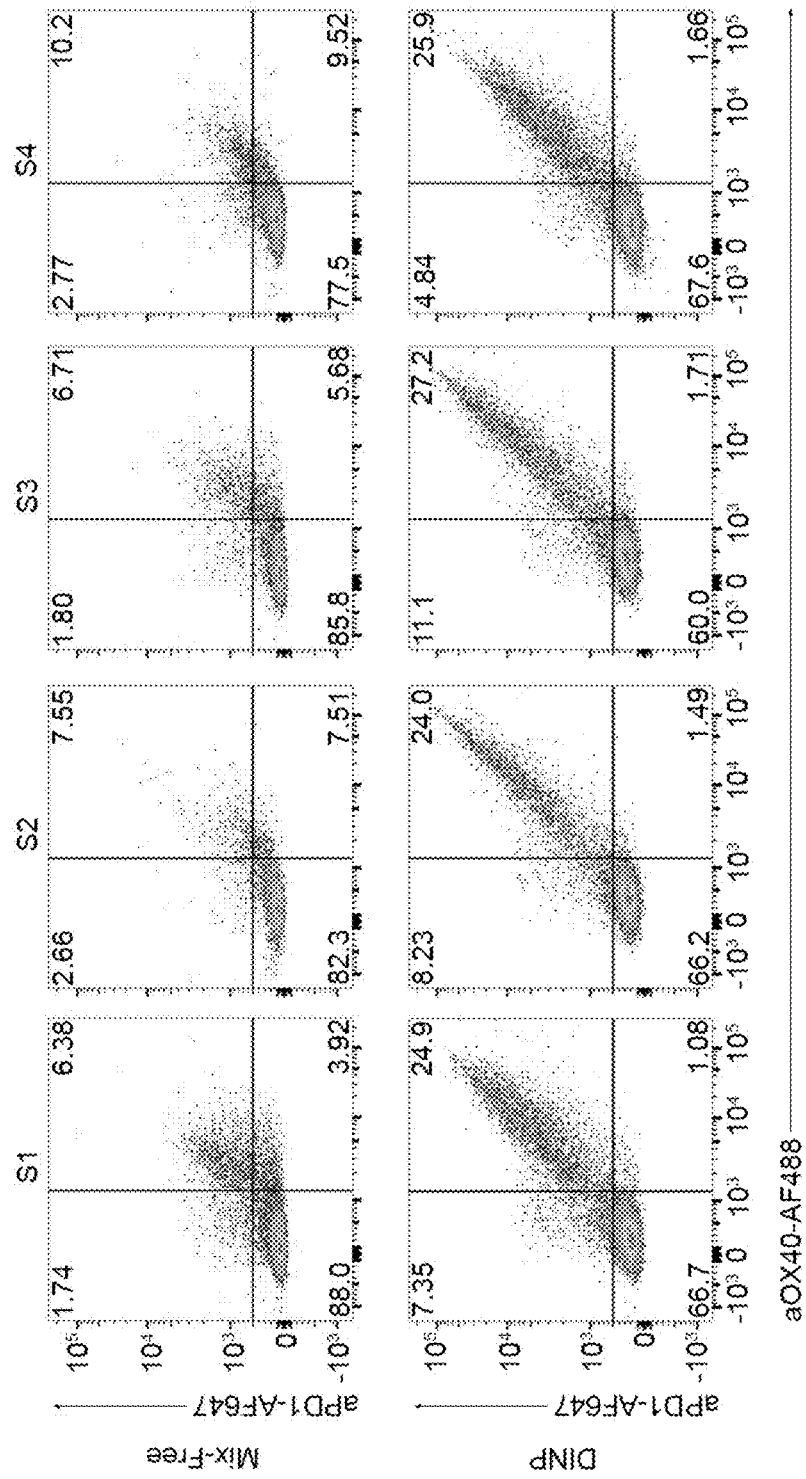
FIGS. 13A-D: DINP improves simultaneous binding of aPD1 and aOX40 to T cells in spleen and tumor in vivo. (13A, 13B) Flow cytometric analysis quantifying the number of T cells bound to fluorescently labeled aPD1 and aOX40 antibodies following combination immunotherapy administered in the form of free antibodies or DINPs in spleen (a) and tumor (b). T cells were defined as CD3+ CD45+. (13C, 13D) Scatter dot plot with mean±standard error of the mean (SEM) assessing percentage of T cells in spleen (c) and tumor (d) with simultaneous binding to aPD1 and aOX40 by flow cytometric analysis. T cells were defined as CD3+CD45+. Statistical significance was assessed using two-tailed t test (n=4). P<0.01, **P<0.0001.
Figure 13B:
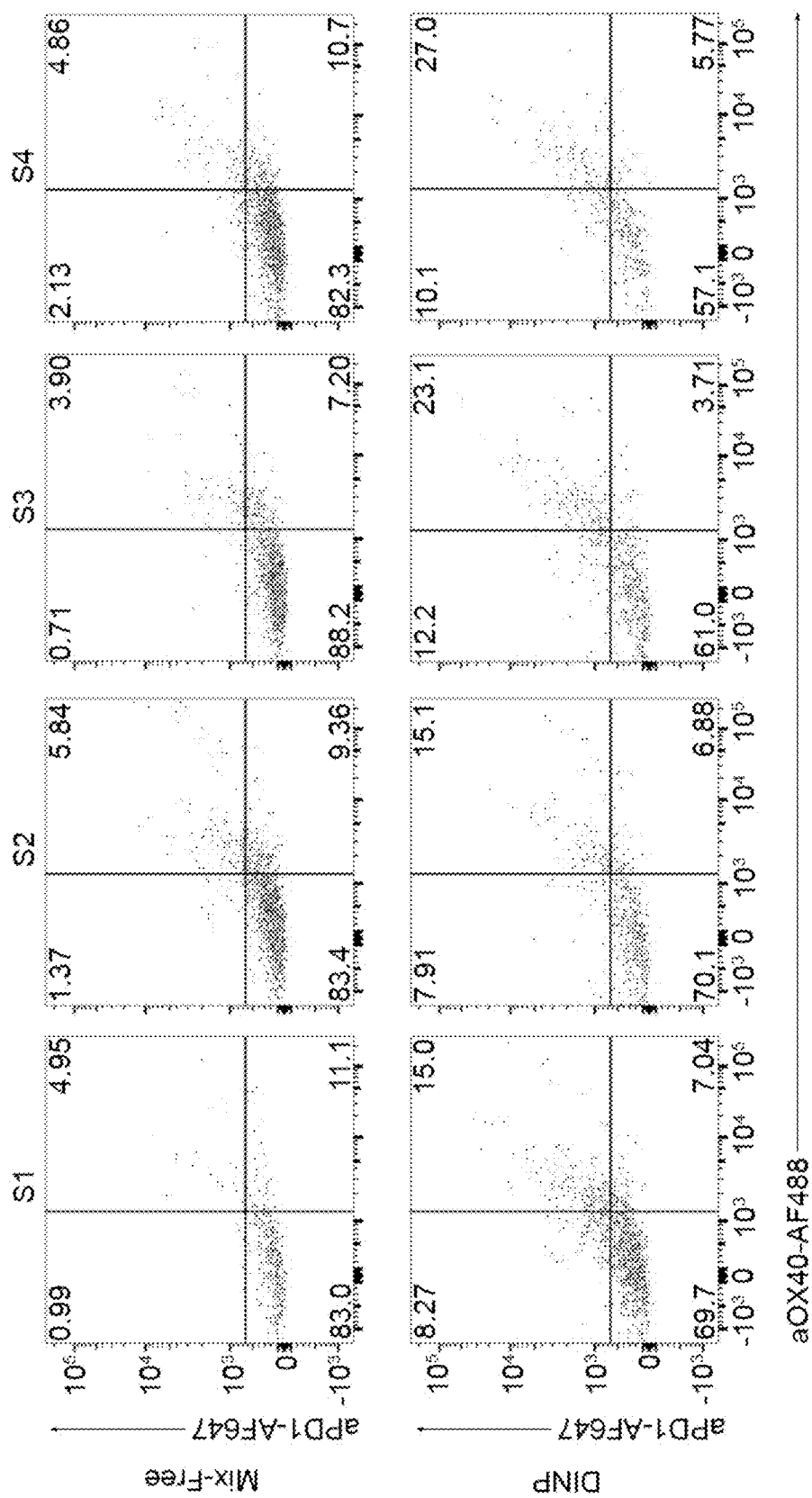
Figure 13C:
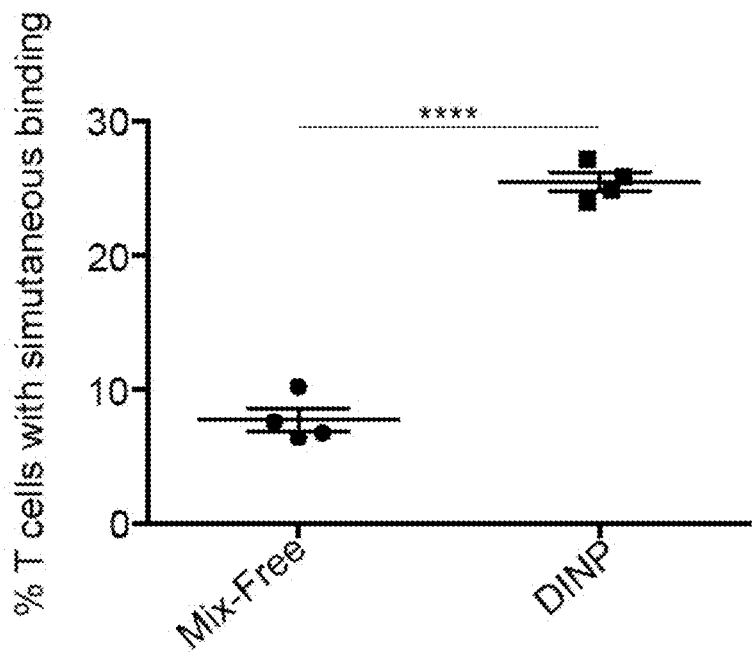
Figure 13D:
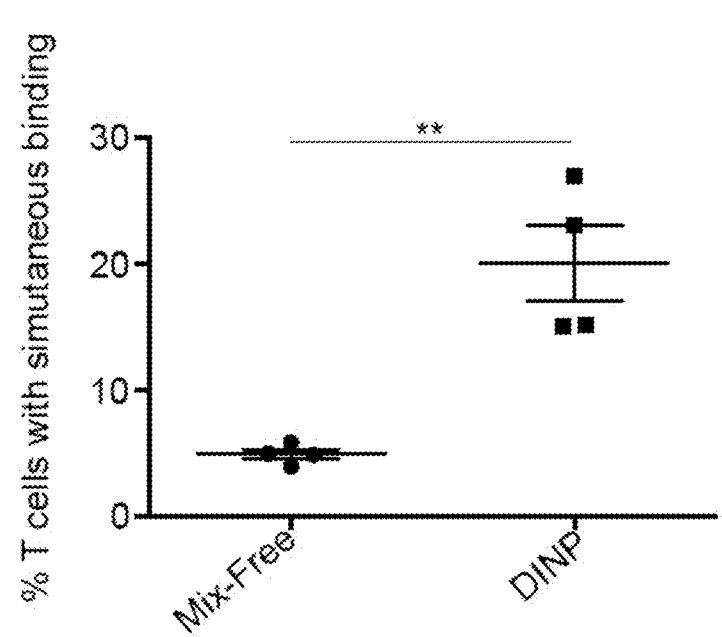
Figure 14A:
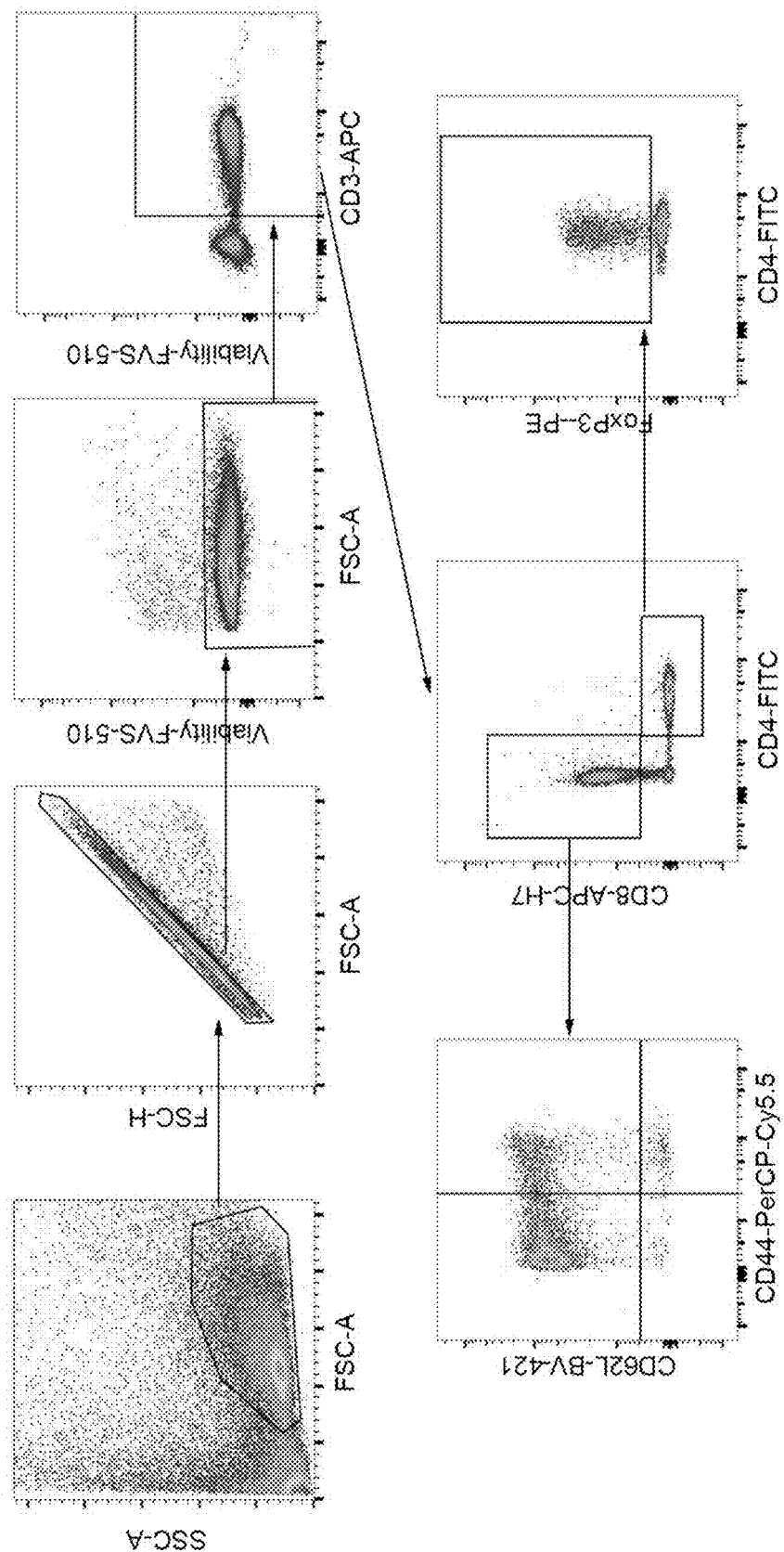
FIGS. 14A-C: Representative flow plots used to quantify the relative abundance of tumor infiltrating T cell subpopulations. (14A) The gating strategy involved identifying the lymphocyte population by forward scatter (FSC) and side scatter (SSC). Single cells were gated by FSC-A and FSC-H. Live (FVS510 viability stain) T cells (CD3+) were gated and then the two main types of T cells were defined by CD4+ T cells and CD8+ T cells. In addition, the CD4+ T cells were further analyzed to identify regulatory T cells (Treg), known as CD4+FoxP3+; the CD8 T cells were analyzed to identify central memory T cells (TCM), known as CD8+CD62L+ CD44+; and effector memory T cells (TEM), known as CD8+CD62L-CD44+, subpopulations. (14B) Representative flow plots used to quantify the relative abundance of tumor infiltration CD4+ and CD8+ T cell subpopulations after different treatments. (14C) Representative flow plots used to quantify the relative abundance of tumor infiltration regulatory T cell subpopulations after different treatments.
Figure 14B:
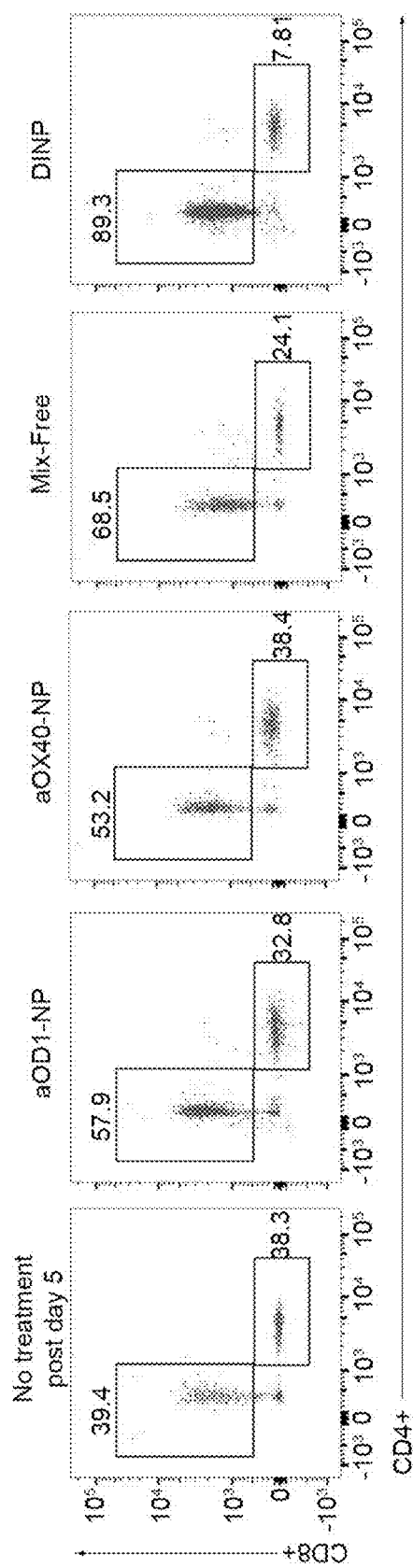
Figure 14C:
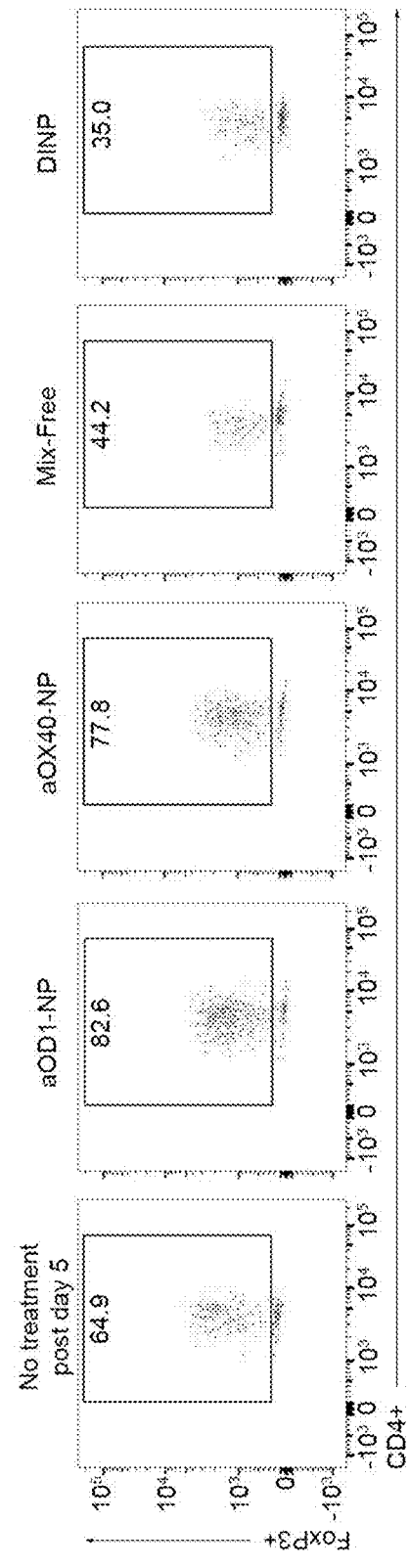

To confirm that the improved immunotherapy is attributed to the simultaneous binding by DINP rather than to NP delivery effects, we assessed the therapeutic efficacy of aPD1-NP plus free aOX40, aOX40-NP plus free aPD1, and DINP in the B16F10 melanoma tumors model. As seen in FIGS. 12A-12B, DINP demonstrated the highest response rate (100%) and significantly better than aOX40-NP plus free aPD1 in tumor inhibition. The survival curve showed that the tumor-free survival rate after DINP's treatment was 30%, compared to 10% after the treatment by aPD1-NP plus free aOX40 or by aOX40-NP plus free aPD1. Taken together, these data suggest that DINP enhances combination immunotherapy.

We next sought to determine the mechanism by which DINP augments the antitumor immune response. First, we compared the relative number of T cells simultaneously receiving aPD1 and aOX40 therapy following DINP versus free antibody therapy. Immune-primed animals bearing bilateral B16F10 tumors were given fluorescently labeled DINPs or fluorescently labeled free antibodies. T cells in spleen and tumor were harvest two hours post therapeutics administration. Using flow cytometry, we compared the number of T cells that possess both fluorescence label between the DINP and free antibody treatment arms (FIGS. 13A-13D). We found that DINP treatment provided a significantly higher percentage of T cells with both aPD1 and aOX40 binding in total T cell population when compared to free antibody treatment, either in spleen (25.5±0.7% vs. 7.7±0.9%) or in tumor (20.1±3.0% vs. 4.9±0.4%).

To determine if DINP-mediated co-delivery of aPD1 and aOX40 translates into increased T-cell activation and expansion in vivo, we quantified the overall number of tumor infiltrating T-cells in B16-F10-bearing animals treated with various immunotherapeutic regimens. Mice treated with DINP had a significantly higher number of CD8+ T-cells (median=85.2%) compared to other treatments, including mixture of free aPD1 and aOX40 (median=68.5%) (FIGS. 4C, 14A-14C). This finding was further validated by immunoflourescence microscopy imaging of excised tumors. Furthermore, DINP treatment increased the ratio of CD8+ to regulatory T-cells infiltrating the tumor (median=19.0) compared to free antibody therapy (median=6.9), which has been shown to be an important prognostic marker for survival in human melanoma (FIG. 4D). Of total CD8+ T-cells, the median frequency of effector memory T-cells among DINP-treated animals was 97.5%, compared to 96.0% in dual antibody-treated animals. Additionally, the ratio of effector memory to central memory T-cells was significantly higher among DINP-treated animals (median=54.4) compared to free antibody-treated animals (median=23.0). Taken together, this higher effector memory frequency and increased effector- to central-memory ratio observed in DINP-treated animals is suggestive of an antigen-driven T-cell response with greater ongoing anti-tumor effector activity among the tumor infiltrating T-cell population.

To confirm that DINP-mediated enhancement of combination immunotherapy is attributable to increased activation of CD8+ T cells, we evaluated DINP treatment in CD8+ T-cell depleted B16-F10-bearing animals (FIGS. 7A-7C). Anti-CD8 depleting antibodies were administered to immune-primed B16F10-bearing animals prior to DINP treatment. We found that CD8+ T-cell depletion resulted in near-complete abrogation of DINP treatment efficacy. In contrast, the effect of NK cell depletion using anti-NK1.1 on DINP efficacy was significantly less pronounced compared to the CD8 depletion. These data suggest that DINP's effect is primarily through CD8+ T-cells and the cytotoxic capacity of the adaptive immune system. Taken together, our data show that combination immunotherapy given in the form of DINP improves treatment response and antitumor immunity by increasing antigen-driven T-cell activation and effector function, resulting in a more immunoreactive tumor microenvironment.

In summary, we demonstrate that co-delivery of synergistic immunotherapeutics using NPs can improve the treatment response of combination immunotherapy. We showed that DINP induces higher T-cell activation than free antibody immunotherapeutics. Importantly, we demonstrated that DINP was significantly more effective than free antibody therapeutics or single therapeutic NPs. While current research is focused on the development of new immunotherapeutics, our work shows that we can significantly improve treatment efficacy through NP delivery. This work carries important implications for cancer immunotherapy as it details a novel strategy and can result in a new class of highly effective immunotherapeutics.

Experimental Section

In vivo binding study. In the binding study, 100,000 B16-F10 cells were suspended in DMEM, mixed with an equal volume of Matrigel (BD Biosciences), and subcutaneously injected on the left flank of C57BL/6 mice on day 0 and the right flank on day 1. 200-µg αPD-1 was intraperitoneally injected into animals on day 7. The left flank tumors were irradiated with 10 Gy on day 8 using a X-RAD 320. A lead shield protected the rest of the animal. Antibodies were first labeled using an AF488 (anti-OX40) or AF647 (anti-PD1) protein labeling kit and then conjugated to the NPs by the same procedure for preparation of DINPs. Fluorescence-labeled DINPs or the mixture of fluorescence-labeled antibodies (200 µg anti-PD1 and 200 µg anti-OX40 in 200 µL PBS) were injected intravenously on day 9. Mice were sacrificed 2 hours later. Tissues were homogenized using the GentleMACs Dissociator and the samples were passed through a 70 µM cell strainer, followed by homogenization by using a 5 mL syringe plunger. The samples were centrifuged for 7 minutes at 1200 RPM, 4° C., decanting the supernatant. Samples were washed and resuspended in cold DPBS and transferred onto a 96 well V-bottom plate. Cells were resuspended in FVS510 viability stain (1:1000 dilution in 200 µL DPBS) for 40 minutes on ice. Wells not receiving viability staining were resuspended in DPBS. Cells were washed twice in staining buffer (0.02% NaN3, 2% BSA in DPBS), resuspended in 100 µL Fc block (1:50 dilution in staining buffer), and incubated on ice for 15 minutes. Antibody master mix was added to samples at 100 µL per sample with final antibody concentrations of:

CD3e BV421 (1:100)
CD45 BV786 (1:100)

Cells were incubated on ice for 45 minutes and washed twice with staining buffer and read out on a BD LSRFortessa flow cytometer. FlowJo flow cytometry software Version 10 was used for analyses.

The foregoing is illustrative of the present invention, and is not to be construed as limiting thereof. The invention is defined by the following claims, with equivalents of the claims to be included therein.

TABLE 1

Optimization of DINP conjugation chemistry

| Sample | Incubation Condition* | [Incubation] (ug/mL) [aPD1]:[aOX40] | Feeding Ratio | [Conjugation] (ug/mg NP) [aPD1] | [aOX40] | Conjugation Ratio |
|---|---|---|---|---|---|---|
| S1 | 1 | 100:100 | 1:1 | 4.9 ± 2.2 | 22.5 ± 6.3 | 0.2:1 |
| S2 | 1 | 200:20 | 10:1 | 28.8 ± 4.5 | 11.3 ± 2.6 | 2.5:1 |
| S3 | 2 | 100:100 | 1:1 | 8.2 ± 3.5 | 26.7 ± 3.3 | 0.3:1 |
| S4 | 2 | 200:100 | 2:1 | 36.8 ± 6.7 | 21.3 ± 6.3 | 1.7:1 |
| S5 | 3 | 200:100 | 2:1 | 49.1 ± 5.5 | 44.0 ± 6.0 | 1.1:1 |
| S6 | 4 | 200:200 | 1:1 | 44.6 ± 4.7 | 54.9 ± 3.4 | 0.8:1 |

Incubation Conditions:
*[1]NPs were co-incubated with aPD1 and aOX40 for 4 h at RT
*[2]NPs were incubated with aPD1 at RT for 2 h and prior to an additional 2 h co-incubation with aOX40 at RT
*[3]NPs were co-incubated with aPD1 and aOX40 for 18 h at 4° C.
*[4]NPs were incubated with aPD1 at RT for 2 h and prior to an additional 18 h co-incubation with aOX40 at 4° C.

TABLE 2

| List of antibodies used for flow cytometric analysis | | | |
|---|---|---|---|
| Antibody | Clone | Fluorophore | Vendor |
| CD3e | 145-2C11 | APC | BD Biosciences |
| CD4 | RM4-5 | FITC | BD Biosciences |
| CD8α | 53-6.7 | APC-H7 | BD Biosciences |
| CD44 | IM7 | PerCP-Cy5.5 | BD Biosciences |
| CD62L | MEL14 | BV421 | BD Biosciences |
| FoxP3 | R16-715 | PE | BD Biosciences |
| CD3e | 145-2C11 | BV421 | BD Biosciences |
| CD45 | 30-F11 | BV786 | BD Biosciences |
| CD16/CD32 (Fc Block) | 2.4G2 | | BD Biosciences |

That which is claimed is:

1. A particle, which can be a microparticle or nanoparticle, comprising two different targeting agents,
   wherein each of the targeting agents is conjugated directly to the particle's surface,
   wherein the two different targeting agents are not conjugated to each other,
   wherein each of the targeting agents binds to a different protein receptor on a T cell surface, and
   wherein the two different targeting agents are an antagonistic PD-1 antibody or active fragment thereof, and an agonistic OX40 antibody or active fragment thereof, respectively.

2. The particle of claim 1, wherein the antibody or active fragment thereof is selected from the group consisting of a monoclonal antibody, a Fab fragment, a Fab'-SH fragment, a FV fragment, a scFV fragment, a (Fab')$_2$ fragment, and any combination thereof.

3. A composition comprising the particle of claim 1 and a pharmaceutically acceptable carrier.

4. A method of activating a T cell, comprising contacting the T cell with the particle of claim 1 under conditions whereby each targeting agent can bind a different protein receptor on the T cell surface.

5. A method of inducing a T cell immune response, comprising contacting the T cell with the particle of claim 1 under conditions whereby each targeting agent can bind a different protein receptor on the surface of the same T cell.

6. A method of inducing a T cell immune response in a subject in need thereof, comprising administering to the subject an effective amount of the particle of claim 1 under conditions whereby each targeting agent can bind a different protein receptor on the surface of the same T cell.

7. A method of activating T cells in a subject in need thereof, comprising administering to the subject an effective amount of the particle of claim 1 under conditions whereby each targeting agent can bind a different protein receptor on the surface of the same T cell.

8. A method of treating cancer in a subject in need thereof, comprising administering to the subject an effective amount of the particle of claim 1 under conditions whereby each targeting agent can bind a different protein receptor on the surface of the same T cell.

9. The method of claim 8, wherein the cancer is selected from the group consisting of breast cancer, lung cancer, ovarian cancer, gastric cancer, bladder cancer, pancreatic cancer, endometrial cancer, uterine cancer, colon cancer, kidney cancer, esophageal cancer, prostate cancer, colorectal cancer, glioblastoma, neuroblastoma, liver cancer, skin cancer, blood cancer and any combination thereof.

10. The method of claim 8, wherein the subject has been diagnosed with cancer.

11. The method of claim 8, wherein the particle is administered via a route selected from the group consisting of intravenously, intramuscularly, subcutaneously, topically, orally, transdermally, intraperitoneally, intrathecally, intraventricularly, intraorbitally, intranasally, by implantation, by inhalation, by intratumoral, and any combination thereof.

12. The method of claim 8, further comprising a step of administering to the subject an effective amount of a chemotherapeutic agent and/or radiation therapy.

13. The method of claim 8, wherein the subject is a mammal.

14. The method of claim 13, wherein the mammal is a human.

15. The particle of claim 1, wherein the two different targeting agents are conjugated to the nanoparticle by click chemistry.

16. The particle of claim 1, wherein the targeting agent is antibody clone RMP1-14 and/or antibody clone OX-86.

* * * * *